(12) United States Patent
Mayor et al.

(10) Patent No.: US 7,583,364 B1
(45) Date of Patent: *Sep. 1, 2009

(54) HIGH PULSE-ENERGY, EYE-SAFE LIDAR SYSTEM

(75) Inventors: Shane Mayor, Boulder, CO (US); Scott Spuler, Westminster, CO (US)

(73) Assignee: University Corporation for Atmospheric Research, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/804,863

(22) Filed: Mar. 19, 2004

(51) Int. Cl.
*G01C 3/08* (2006.01)
*G01N 21/00* (2006.01)

(52) U.S. Cl. ................................. 356/4.01; 356/337

(58) Field of Classification Search ....... 356/4.01–5.15, 356/28, 301, 337, 342; 359/327
See application file for complete search history.

(56) References Cited

U.S. PATENT DOCUMENTS

| | | | | |
|---|---|---|---|---|
| 3,963,347 | A * | 6/1976 | Segre et al. ................. | 356/5.01 |
| 4,095,121 | A * | 6/1978 | Begley et al. ............... | 359/327 |
| 4,239,995 | A * | 12/1980 | Feldman et al. ............. | 359/327 |
| 4,858,238 | A * | 8/1989 | Cardimona .................... | 372/3 |
| 5,058,117 | A * | 10/1991 | Shoshan et al. ................ | 372/3 |
| 5,090,016 | A * | 2/1992 | Dewhirst et al. ............... | 372/3 |
| 5,241,315 | A | 8/1993 | Spinhirne .................... | 342/54 |
| 5,414,723 | A * | 5/1995 | Krapchev ..................... | 372/3 |
| 5,726,802 | A * | 3/1998 | Stultz ........................ | 359/487 |
| 6,580,732 | B1 * | 6/2003 | Guch et al. ................... | 372/18 |
| 2003/0016350 | A1 | 1/2003 | Cheng et al. ................. | 356/301 |

OTHER PUBLICATIONS

Paper entitled "Counterproliferation Long Range Biological Stand-off Detection System" limited distribution, U.S. Army Soldier and Biological Chemical Command, Aberdeen Proving Ground, MD, Rev. Apr. 26, 2000.

News Release, Contract No. 283-95, Office of Assistant Secretary of Defense (Public Affairs), Washington, D.C., May 23, 1995. http://www.defenselink.mil/news/May1995/c052395_ct283-95.h.

Paper reprinted from the Proceedings of the International Conference on Lasers '97entitled "Generation of 1.54 µm Radiation With Application To An Eye-Safe Laser Lidar" authored by N.A. Kurnit, R. F. Harrison, R. R. Karl, Jr., J. P. Brucker, J. Busse, W. K. Grace, O. G. Peterson and W. Baird of the Los Alamos National Laboratory, Los Alamos, NM, and W. S. Hungate of the U.S. Army CBDCOM, Aberdeen Proving Ground, MD., pp. 608-610.

(Continued)

*Primary Examiner*—Isam Alsomiri
(74) *Attorney, Agent, or Firm*—Marsh Fischmann & Breyfogle LLP

(57) ABSTRACT

An eye-safe atmospheric aerosol lidar featuring high transmit pulse energy to generate strong backscatter from long ranges in a single pulse together with an optically efficient receiver is disclosed. The transmitter employs a gas cell and non-focused laser beam geometry to convert short wavelength laser light to substantially safer and longer wavelength light by stimulated Raman scattering. The longer wavelength light is substantially safer than the shorter wavelength light thereby allowing the safe transmission of high energy pulses. The transmitter also features a diode injection seed and a beam expander which are effective to reduce the divergence of the long wavelength light below the field-of-view of the receiver. The receiver employs a telescope, collimating lens, interference filter, focusing lens, avalanche photodiode detector, amplifier and analog to digital converter. The transmit beam and receiver field of view are coaxial. Initial results demonstrate the ability of such technology to elucidate the structure of the atmosphere with high temporal and spatial resolution.

24 Claims, 13 Drawing Sheets

OTHER PUBLICATIONS

Datasheet titled "C30659E-900-1060-1550 nm Series Silicon and InGaAs APD Preamplifier Modules", www.perkinelmer.com/optoelectronics, pp. 1-9.

Paper entitled "M-Squared Laser Beam and Telescope Overlap Factors for a 1.55 micron KTP OPO Lidar", by Priyavadan Mamidipudi and Dennis Killinger, Dept. of Physics, Univ. of So. Fla., Tampa, Florida, pp. 837-840.

Paper entitled "Optimal Detector Selection for a 1.5 micron KTP OPO Atmospheric Lidar", by Priyavadan Mamidipudi and Dennis Killinger, Univ. of So. Fla., Tampa, Florida, part of the SPIE Conference on Laser Radar Technology andApplications IV, Orlando, Florida, Apr. 1999 [SPIE vol. 3707—0277-786X/99], pp. 327-335.

Paper entitled High-Energy, Eyesafe Lidar for Long-Range, High-Resolution Aerosol Detection [NASA Langley Phase II SBIR, Contract NAS1-20476], pp. 1-5, Mar. 8, 2002.

Paper entitled "Boundary Layer Height Measurements with an Eyesafe LIDAR", by G. G. Gimmestad, E. M. Patterson, D. W. Roberts and S. C. Gimmestad, Electro-optics, Environment and Materials Laboratory, Georgia Tech Research Institute, Georgia Institute of Technology, Atlanta, Georgia, SPIE vol. 2112, pp. 187-193.

Article entitled "A Powerful Eyesafe Infrared Aerosol LIDAR: Application of Stimulated Raman Backscattering of 1.06 μm radiation", W. Carmuth and T. Tricki, Rev. Sci. Instrum. 65 (11), Nov. 1994, copyright 1994 American Institute of Physics.

Applied Optics, vol. 28, No. 23, Dec. 1, 1989, pp. 4978-4981, article "Initial Measurements using a 1.54- μm Eyesafe Raman Shited Lidar", Edward M. Patterson, David W. Roberts nd Gary G. Gimmestad, Georgia Institute of Technology, Atlanta, Georgia.

Paper entitled "Compact, Ruggedized Eyesafe Laser Transmitter", J. C. McCarthy, P. A. Ketteridge, R. Day, Ian Lee and Evan Chicklis, pp. 617, 618.

Lidar Remote Sensing for Industry and Environment Monitoring II, Upendra N. Singh, Editor. Proceedings of SPIE vol. 4484 (2002) copyright SPIE: "Design Validation of an Eye-Safe Scanning Aerosol Lidar with the Center for Lidar and Atmospheric Sciences Students (CLASS) AT Hampton University", by Dale A. Richter, N. Scott Higdon, Patrick Ponsardin and David Sanchez, Itt Industries, Albuquerque, NM and Thomas H. Chyba, Doyle A. Temple, Wei Gong, Russell Battle, Mika Edmondson, Anne Futrell, David Harper, Lincoln Haughton, Demetra Johnson, Kyle Lewis and Renee S. Payne-Baggott, Center for Lidar and Atmospheric Sciences Students, Hampton University, Hampton, VA.

Applied Optics, May 20, 1997, vol. 36, No. 15: "Aerosol and cloud backscatter at 1.06, 1.54, and 0.53 μm by airborne hard-target-calibrated Nd:YAG/methane Raman lidar", by James D. Spinhirne, S. Chudamani, John F. Cavanaugh and Jack L. Bufton, pp. 3475-3490, copyright 1997 Optical Society of America.

Optical Engineering, vol. 35 No. 12, Dec. 1996, pp. 3579-3584: "Comparison of Raman and degenerated optical parametric oscillators for a high-energy and high-repetition-rate eye-safe laser", by Gilles Roy and Pierre Mathieu.

"Atmospheric Laser Radar Measurements Using Two Novel, Eye-Safe Infrared Optical arametric Oscillators", a dissertation submitted by Sarah Rhodes Harrell, Dec. 1995, Departments of Physics and Electrical Engineering, University of South Florida.

Report entitled "Final Report on High-Energy, Eyesafe Lidar for Long-Range, High-Resolution Aerosol Detection." Prepared for NASA Langley Research Center, Hampton, VA. Contract: NAS1-20476 (Phase II SBIR). Reporting Period: Mar. 22, 1995-Dec. 31, 1997. Report prepared by: Schwartz Electro-Optics, Inc., Research Division, Bedford MA.

* cited by examiner

HIGH PULSE-ENERGY, EYE-SAFE LIDAR SYSTEM

GOVERNMENT SUPPORT

The invention was made with Government support under Cooperative Agreement No. ATM-9820037 awarded by the National Science Foundation. The Government has certain rights in this invention.

FIELD OF THE INVENTION

This invention relates to laser radars or lidars in general and more particularly to an eye safe lidar suitable for scientific and commercial applications requiring long range and strong backscatter from a single or a small number of laser pulses such as scanning applications.

BACKGROUND OF THE INVENTION

Lidar has been an atmospheric research tool for over thirty years and within the last decade commercial systems have become available. Generally, these systems transmit laser energy into the atmosphere and detect backscattered radiation for analysis to identify particle aggregations and atmospheric structure of interest. Such systems have the potential to enable identification and imaging of aerosols, aerosol structures and the like at long distances through the atmosphere. Such information may be used, for example, by meteorologists to analyze atmospheric structure, by regulatory bodies to monitor atmospheric emissions or by security organizations to identify and track the source of harmful agents in the atmosphere.

In order to provide effective imaging, particularly for long-range applications, significant transmitted laser energy and significant associated backscatter energy are desired. However, transmission energy levels are limited by eye-safety considerations. In this regard, various standards bodies in various jurisdictions have developed standards applicable to the transmission of laser energy into the atmosphere. Commercial systems generally achieve eye-safety by transmitting many (greater than 1000 per second) very weak (less than 10 micro-joule) pulses. This approach is known as the "micropulse technique" and it requires receivers with photon counting capability. To obtain useful data however, micropulse systems require the integration of backscattered signal energy from many laser pulses. This requirement is not desirable for applications requiring high temporal and/or spatial resolution such as scanning.

The noted eye-safety standards define maximum eye-safe energies as a function of, among other things, the wavelength of an optical beam. For example, in the visible portion of the spectrum where light is focused onto the retina by the lens, allowable energies are low. In the ultraviolet portion of the spectrum allowable energies increase. Unfortunately, shorter wavelengths generate stronger molecular (Rayleigh) backscattering which competes for the dynamic range of the receiver. Allowable energies also increase in the infrared portion of the spectrum, but receiver efficiencies decrease at longer wavelengths. For these reasons, it is highly preferable for an aerosol backscatter lidar to operate in the near-infrared portion of the spectrum.

The 1.5 to 1.8 micron band of the spectrum has the highest maximum permissible exposure for the human eye in the optical electromagnetic spectrum. This is because the energy is absorbed volumetrically within the eye whereas at longer and shorter wavelengths it is absorbed in the surface tissue or focused onto the retina. Therefore, by operating in this wavelength region it is possible to safely transmit a higher magnitude of pulse energy. Unfortunately, there are considerable difficulties associated with generating the desired high pulse energy, low divergence beams, constructing optically efficient receivers and developing optically efficient system architectures in this wavelength range.

SUMMARY OF THE INVENTION

The present invention relates to a lidar system and system components for enabling long range and/or high temporal resolution atmospheric analyses. In particular, the invention includes a transmitter that enables transmission of high pulse energy, eye-safe beams with minimal divergence. Additionally, a high optical efficiency, high range resolution receiver is provided. The invention also enables lidar system applications requiring a long range, high spatial and temporal resolution lidar system such as scanning and volume imaging applications.

It has been recognized that system optimization for various lidar applications depends on achieving improved temporal resolution. That is, sufficient backscatter energy to support the desired analysis, e.g., imaging or particle characterization, needs to be obtained within a reasonably short time window. For example, in order to image a substantial volume of the atmosphere with a desired resolution by obtaining multiple images, and to accomplish such volume imaging within a time period where structures to be imaged are not dramatically changed, it is desirable to be able to acquire individual images in a short time period. Moreover, in order to avoid spatial smearing (degradation of angular resolution) in continuous scanning applications, substantially instantaneous data acquisition is desirable. High temporal resolution is also useful for accurately monitoring structural changes over time.

Such applications demand high temporal resolution which, ideally, involves obtaining useful information from a single or at least a small number of beam pulses. Some of the considerations that may be addressed in this regard include: 1) optimizing the transmitter to provide a high pulse energy while maintaining eye safety; 2) optimizing the transmitter to provide low beam divergence; 3) optimizing the transmitter to provide a high pulse repetition frequency; 4) optimizing the receiver to provide high range resolution (high bandwidth); 5) optimizing the receiver to provide high optical efficiency in mapping backscattered radiation to a high gain detector medium; 6) optimizing system design so that the transmitted beam is substantially fully within the receiver's field of view, with respect to the range of interest, for enhanced optical efficiency; and 7) matching the beam divergence to the field of view for enhanced noise rejection. Many other considerations—including practical issues such as system robustness, low maintenance and leveraging of existing technologies developed for other fields—may be taken into consideration. Accordingly, achieving high temporal resolution involves a number of parameters at the component and system levels. Identifying and addressing these issues provides a significant motivation related to the various aspects of the invention as set forth below.

In accordance with one aspect of the present invention, a lidar system is provided where the transmitter properties are coordinated with the receiver properties to achieve desired performance characteristics. In this regard, due to the desired high range resolving capabilities of a lidar, it is preferred to use fast response (high bandwidth) photodetectors. In the 1.5-1.8 wavelength region, a practical and cost effective option is detectors using indium gallium arsenide (InGaAs)

as an active gain medium. To maintain high speed (high bandwidth) the active areas of these detectors are generally small—typically 200 microns in diameter. This small area, when projected through an optimized lidar receiver system as discussed below, subtends a very narrow field-of-view in the atmosphere.

With regard to the transmitter, transmitted photons that do not illuminate the receiver's field of view are wasted. Therefore, an efficient lidar system preferably utilizes a transmit beam with divergence less than or nearly matched to the receiver's field of view over the desired range. For Gaussian beams, it may be desired to provide a field of view somewhat in excess of the beam divergence, though near matching may be desired for improved ambient noise rejection and enhanced detector speed. In the 1.5-1.8 micron band, this represents a significant challenge because of the small detectors desired for improved range resolution. The small detectors thus drive the requirement for laser beams at this wavelength with low divergence. It is further noted in this regard that the maximum eye-safe energies are also a function of beamwidth (diameter), which in turn drives the requirement for an optically efficient receiver.

Thus, a lidar system according to this aspect of the invention includes a transmitter for transmitting a beam with a nominal wavelength (e.g., a center wavelength) between about 1.5-1.8 microns and a first value of divergence over a range of interest (e.g., 500 m to 5 km), and a receiver for receiving backscattered radiation of the beam having a second value of field of view (FOV), where the second value is at least about equal to the first value. The half angle FOV of the receiver in this regard can be given by the detector radius divided by the focal length of the receiver. In one implementation, the divergence of the transmitted beam is 0.20 by 0.24 mrad and the receiver FOV is 0.27 mrad. A corresponding method involves transmitting a beam having a wavelength of between about 1.5-1.8 microns and a first value of divergence and receiving the beam using a receiver having a second value of FOV at least about equal to the first value.

In accordance with another aspect of the present invention, a scanning lidar is provided for operation in the wavelength range of between about 1.5-1.8 microns. The system includes a transmitter for transmitting a beam of the noted wavelength, a receiver for receiving backscattered radiation of the beam, and a scanner for scanning the transmitted beam across a range of interest. In this regard, the range of interest may be defined by an angular range relative to one or more axes. For example, to map aerosols in the atmosphere, the beam may be scanned, for example in a raster pattern, across azimuth and elevation ranges defining a hemisphere. Such scanning may be continuous (proceeding unidirectionally over multiple scans of an angular range defining a circle) or cycling (including a scanning direction change) with respect to each axis. A slip ring or similar structure may be provided in this regard to accommodate continuous scanning.

As noted above, high temporal resolution may be desired for scanning operation to avoid angular smearing. Preferably, the lidar system has a temporal resolution of 1 second or less in this regard. In addition, a high sampling frequency may be desired to enable completion of a scan with a desired scanning resolution or within a desired time period. In one implementation, the temporal resolution and sampling frequency correspond to a single pulse of a transmitter having a pulse length of no more than about 10 ns and a pulse repetition frequency of at least about 10 Hz.

A corresponding method involves operating a transmitter to transmit a beam having a wavelength of between about 1.5-1.8 microns, scanning the beam across a range of interest, and operating a receiver to receive the beam during the scan. The receiver is preferably scanned in coordination with the transmitter. A processor may be operated to construct a composite image corresponding to at least a portion of a scan cycle.

In accordance with a further aspect of the present invention, a ground-based transmitter and corresponding methodology are provided for transmitting low divergence beams into the atmosphere. The transmitter includes a laser pump for generating a source beam having a first nominal wavelength, beam directing optics for directing a wavelength shifted beam from near ground elevation into the atmosphere (vertically or otherwise), and a beam processor interposed between the laser pump and the beam directing optics. The beam processor includes a wavelength shifter for providing the wavelength shifted beam and optics for conditioning the wavelength shifted beam. The wavelength shifted beam has a nominal wavelength of between about 1.5-1.8 microns and a divergence of less than about 0.5 mrad and, preferably, less than about 0.25 mrad.

In one implementation, the laser pump provides a source beam having a wavelength of about 1064 nm. The wavelength shifter is preferably a non-solid-state device, for example, including a Raman cell. The conditioning optics may include a beam expanding device, such as in the form of a Galilean telescope, to achieve a desired beam divergence and/or optical density.

In accordance with a still further aspect of the present invention, a ground based transmitter is provided for transmitting high pulse energy, eye-safe beams with low divergence into the atmosphere. The transmitter includes a laser pump for generating a source beam having a first nominal wavelength, beam directing optics for directing a processed beam from near ground elevation into the atmosphere, and a beam processor operatively interposed between the laser pump and the beam directing optics. The beam processor is operative for modifying at least one of a wavelength and a beamwidth of the source beam to produce the processed beam. The processed beam has a pulse energy of at least 100 mJ/pulse, a divergence of no greater than 0.5 mrad and an energy within the eye safety standards of the American National Standard for the Safe Use of Lasers ANSI Z136.1-2000, which is incorporated herein by reference. In one implementation, the beam processor includes a wavelength shifter, for example, including a Raman cell, and a beam spreader, for example, in the form of a Galilean telescope. It will be appreciated that such high pulse energy, eye-safe beams with low divergence facilitate the operation of lidar systems having high temporal resolution and high optical efficiency.

According to another aspect of the present invention, a Raman shifted transmitter is provided for ground-based or airborne applications. The transmitter includes a laser pump for generating a pulsed source beam having a first nominal wavelength and a first pulse energy, and a Raman cell system for providing a wavelength shifted pulse beam. The Raman cell has a pressure of no more than about 15 atm and, preferably, no more than about 10 atm. The wavelength shifted pulse beam has a second pulse energy that is at least about 25% of the first pulse energy and, preferably, greater than 30% of the first pulse energy.

In one implementation, the Raman cell system includes a methane cell. Optics are provided within the methane cell to define a folded optical path for gas illumination. The optics may include at least one internal reflectance element such as a prism for improved gas illumination and improved robustness in relation to surface reflectors. The source beam preferably has a high optical density for enhanced wavelength shifting efficiency but is not tightly focused, thereby reducing sooting sometimes associated with methane cells. For example, the pump laser may provide an 800 mJ/pulse energy beam at 1064 nm wavelength having a diameter of approximately 9 mm. A beam compressor, for example in the form of a Galilean telescope, may be provided between the pump laser and the Raman cell to compress the beam diameter, for example, to approximately 6 nm in diameter.

The beam processor may further include a beam expander and an optical filter disposed between the Raman cell system and the beam directing optics. The beam expander, which may be provided in the form of a Galilean telescope, allows for expansion of the wavelength shifted beam so as to achieve a desired divergence and/or optical density. The wavelength filter is provided to ensure that the transmitted beam is eye-safe. In this regard, the beam exiting the Raman cell will generally include an eye-safe wavelength shifted component and a component at the laser pump wavelength. It is generally desired to transmit only the eye-safe component into the atmosphere. Accordingly, the filter preferably removes at least the laser pump component. In this regard, the filter may include a component, such as a prism, for spatially separating the components on a wavelength dependent basis and a blocking element for selectively transmitting only the eye-safe component. For example, the unsafe component may be directed into a black box or other optical absorber.

In accordance with a still further aspect of the present invention, a high range resolution receiver is provided, for example, for use in an atmospheric aerosol lidar system. As discussed above, atmospheric aerosol lidar systems desirably have a range extending from near the receiver (e.g., 500 m or less) to greater than 5 km and, preferably, greater than 10 km. Such systems also desirably have a high range resolution, e.g., a range resolution of no more than about 50 m and, preferably, less than 10 m. The present aspect of the invention provides a receiver including collection optics for receiving backscattered radiation and collecting the radiation into a compressed beam, a detector for converting incident radiation into an electrical signal representative of the incident radiation, and focusing optics interposed between the collection optics and the detector for receiving the compressed beam and focusing the beam onto a photoactive surface of the detector. In one embodiment for 1.5-1.8 micron wavelength applications, the detector is an InGaAs detector having a diameter of about 200 microns and a bandwidth of 200 MHz, thus providing a theoretical range resolution of 30 cm.

In accordance with another aspect of the present invention, a high range resolution, low FOV receiver is provided, for example, for use in atmospheric aerosol lidar systems. A defined FOV may be desired to match the receiver to the transmitter for improved noise rejection, and a reduced FOV allows for system optimization in relation to low divergence beam applications. The receiver of this aspect of the invention thus includes collection optics having a defined focal length and an active detector surface having a radius or semi-major axis ("detector dimension"), where the FOV (calculated as the detector dimension divided by the focal length of the collection optics) is less than 0.5 mrad and the receiver has a range resolution of no more than 50 m and, preferably, less than 10 m. For example, the collection optics may include a telescope optically coupled to a small radius, high bandwidth detector.

In accordance with a further aspect of the invention, an optically efficient receiver is provided for receiving 1.5-1.8 micron wavelength radiation. The receiver includes a telescope optically coupled to a detector for converting 1.5-1.8 micron wavelength radiation into an electrical signal. For example, the detector may be a InGaAs detector. The telescope has a transmissivity of at least about 70% for the 1.5-1.8 micron wavelength range, and preferably, has a transmissivity of at least 85%. For example, the telescope may be a Schmidt-Cassegrain telescope or a Newtonian telescope. In either case, the telescope preferably includes mirror surfaces coated for improved transmissivity in the target wavelength range.

BRIEF DESCRIPTION OF THE DRAWINGS

For a more complete understanding of the present invention and further advantages thereof, reference is now made to the following Detailed Description taken in conjunction in with the drawings, in which.

DETAILED DESCRIPTION OF THE INVENTION

In the following description, the invention is set forth in the context of a high pulse energy, and Raman shifted Eye-safe Aerosol Lidar (REAL™) system. Indeed, the invention has a number of benefits and provides useful results in this regard. However, it will be appreciated that various aspects of the present invention are not limited to such lidar applications. Accordingly, the following description should be understood as exemplifying the invention and not by way of limitation.

Elastic backscatter lidars are useful tools for atmospheric researchers and potentially for commercial users because they are capable of showing the aerosol distribution in the atmosphere in both space and time. Although the backscatter return from these systems is typically uncalibrated, the images they provide are extremely valuable for identification of boundary layer depth, elevated aerosol layers, wave activity, and sources of pollution. Unfortunately, currently useful atmospheric aerosol lidars are generally not eye-safe within certain ranges of such instruments. This ocular hazard greatly restricts the number of applications and environments in which they can be used. For example, data cannot be collected near airports or in urban areas. Therefore, development of a completely eye-safe aerosol backscatter lidar is a high priority.

Figure 1:
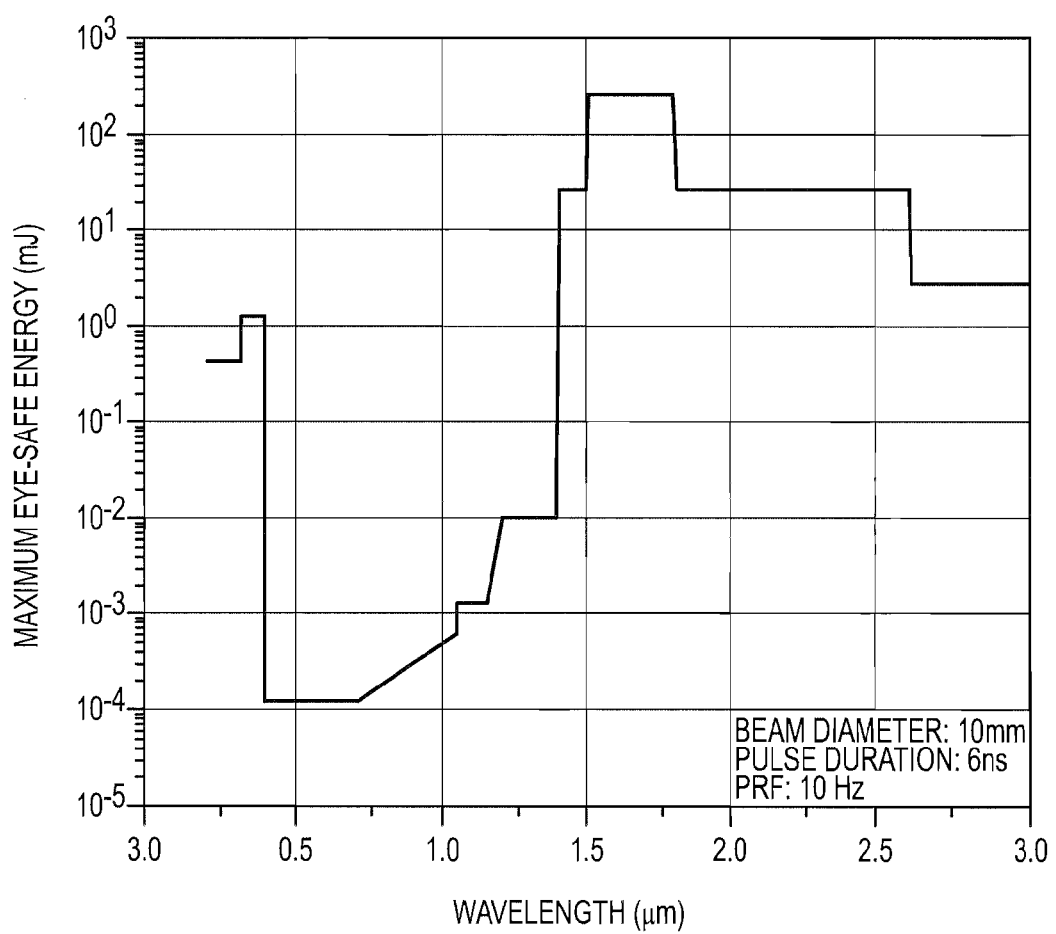
FIG. 1 illustrates the maximum eye-safe energy for a pulse laser according to ANSI standards for particular pulse beam parameters.

There are currently several general approaches for developing an eye-safe lidar. The three broad practical possibilities are: (1) operating at wavelengths less than 0.4 μm, (2) using the micro-pulse technique in the visible part of the spectrum, and (3) operating at wavelengths greater than 1.4 μm. The human eye is particularly vulnerable to wavelengths between 0.4 μm and 1.4 μm because those wavelengths easily pass through the cornea and lens and are focused on the retina. Light at wavelengths less than 0.4 μm and greater than 1.4 μm are safely absorbed in the lens and cornea at the energy densities sufficient for lidar applications. FIG. 1 shows the maximum eye-safe energy (MPE$^2$ times the beam area) for a pulsed laser as a function of beam wavelength. The chart shows that the region between 1.5 and 1.8 microns has the highest permissible energy. With modest beam expansion it is possible to safely transmit over 1 J per pulse in this region.

The maximum eye-safe energy remains modestly high (similar to 355 nm) for wavelengths longer than 1.4 microns; however, photodetector performance decreases with increasing wavelength. Although Doppler lidars at 2 and 10 microns are successful by using a heterodyne detection method, direct detection lidar in the IR is best performed at 1.5 μm due to the availability of inexpensive, high quantum efficiency detectors which do not require cooling. In addition to these factors, work at infrared wavelengths has the advantage over the ultraviolet in that it features low molecular scattering. Backscattering from molecules in undesirable for aerosol lidars because it reduces the contrast between aerosol backscattering and the noise background. The 1.5 micron wavelength region also features lower sky radiance than a broad range of ultra-violet and visible wavelengths thus improving signal-to-noise ration. When compared to visible region, infrared beams are invisible and therefore eliminate the potential of flash blinding pilots or drawing unwanted attention from the public. Lastly, working in this wavelength allows one to take advantage of recent advancements in the telecommunications sector (e.g., detectors, optical coatings, lasers, etc).

There are a few choices for generating pulsed light in the 1.5 micron wavelength region. Solid state methods include optical parametric oscillators (OPOs), solid state resonators employing Er:glass or Cr$^{4+}$:YAG, and stimulated Raman scattering (SRS). The embodiments described in detail below employ SRS for several reasons including robustness of technique, the quality of the resulting beams including low divergence at the desired power for direct-detection lidar and cost effectiveness.

Figure 2:
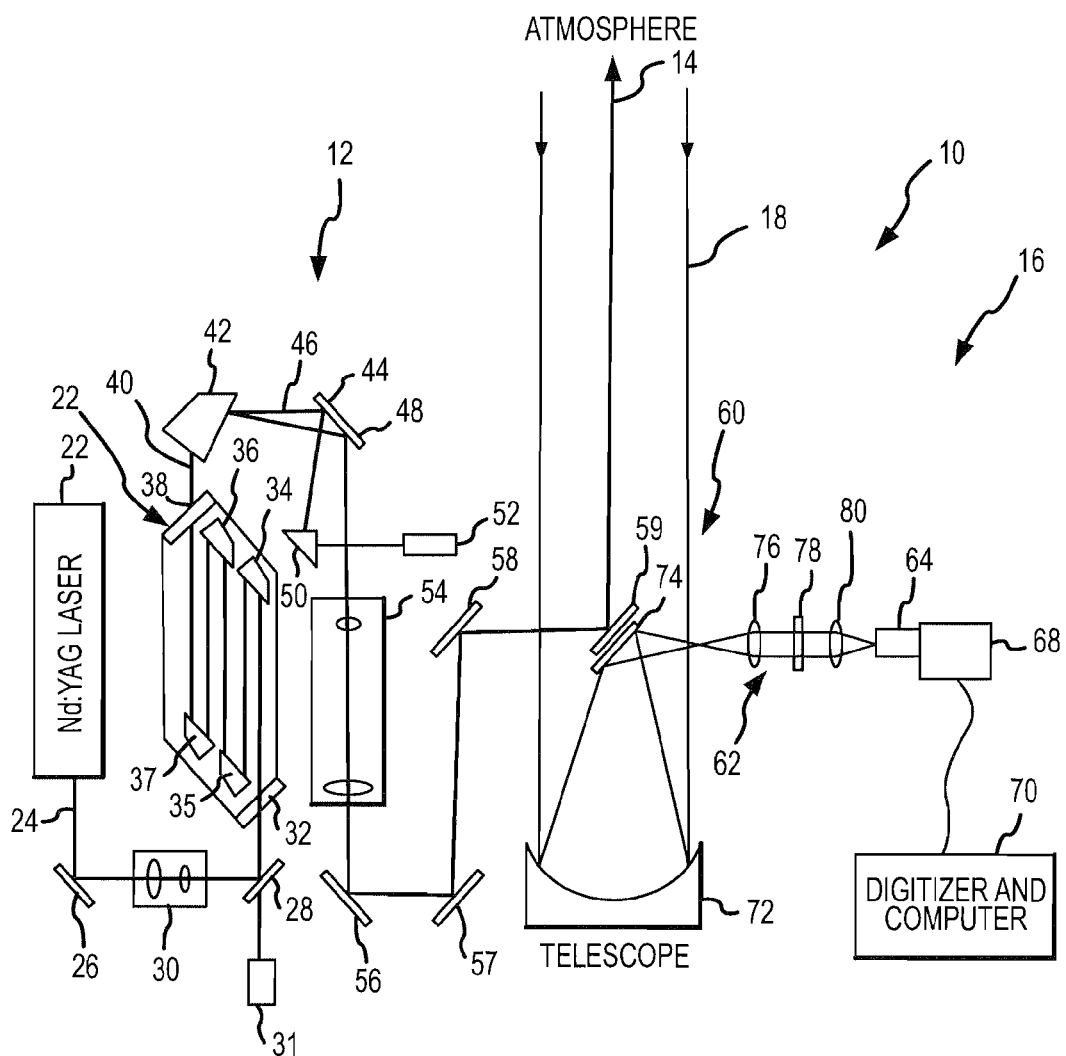
FIG. 2 is a schematic diagram illustrating an atmospheric aerosol lidar system in accordance with the present invention.

FIG. 2 is a schematic diagram of a Raman-shifted eye-safe aerosol lidar (REAL) system 10 constructed in accordance with the present invention. The REAL system 10 generally includes a transmitter 12 for transmitting a low divergence, eye-safe beam 14 into the atmosphere and a receiver 16 for receiving backscattered radiation 18 associated with the transmitted beam 14. The transmitter 12 and receiver 16 are described in turn below.

The transmitter 12 includes, among other things, a source pump laser 20 and a Raman cell 22. As discussed above, beams having desired characteristics within the desired wavelength range can be provided by using certain available pump lasers and then converting the source beam to the desired wavelength range using Raman techniques. In the illustrated embodiment, the pump laser 20 is a flash-lamp pulsed, Q-switched, Nd:YAG laser capable of generating 800 mJ/pulse energy at 1064 nm wavelength. Such a pump laser is marketed under the name Continuum Surelite III. The pump laser 20 produces a flat-topped multiple transverse mode beam with pulses 6 ns full-width half-max (FWHM) in duration. The beam 24 exiting the pump laser 20 is approximately 9 mm in diameter with a divergence of 0.6 mrad. The beam 24 is directed to the Raman cell 22 by way of folding mirrors 26 and 28. As will be discussed below, folding mirror 28 has coating properties so as to allow for transmission of a seed beam through the mirror 28 for coaxial alignment of the seed beam and source beam 24.

The Raman cell 22 is a methane Raman cell that operates to convert the source beam 24 having a wavelength of 1064 nm to a first Stokes wavelength of 1.543 microns within the desired range for eye safety. A principle disadvantage of such Raman cells as heretofore constructed is that the focused beams used in such applications resulted in substantial degradation or sooting of the methane which in turn degrades the optical properties of the system. In order to minimize such sooting, while providing a beam of sufficient optical density for enhanced wavelength conversion, the illustrated transmitter 12 employs a beam reducer 30. The illustrated beam reducer 30 is provided via a small Galilean telescope.

In the illustrated embodiment, the pump beam is converted to the eye-safe wavelength via stimulated Raman scattering (SRS) in a pressurized cell filled with pure $CH_4$. SRS is a third-order, nonlinear, inelastic scattering process whereby a sufficiently-high pump field excites molecular vibrations in a medium. The frequency of the scattered light (Stokes output) is shifted by the frequency of these vibrations. Assuming the pump is not depleted, the Stokes intensity as a function of distance is given by the equation $$I_S(z) = I_S(0) e^{g_R I_p z} \quad (1)$$

in which $I_S(0)$ is the initial Stokes intensity, $g_R$ is the steady state Raman gain coefficient, $I_p$ is the pump intensity, and z is the interaction length. The gain coefficient is a function of the Raman active medium and its pressure.

The nth Stokes $\lambda_n^S$, and anti-Stokes, $\lambda_n^{AS}$, wavelengths are given by $$\lambda_n^S = \left(\frac{1}{\lambda_p} - \frac{n}{\lambda_R}\right)^{-1} \text{ and } \lambda_n^{AS} = \left(\frac{1}{\lambda_p} - \frac{n}{\lambda_R}\right)^{-1} \quad (2)$$

respectively, where $\lambda_p$ is the pump wavelength, and $\lambda_R$ is the wavelength of the Raman transition. The wavelength of the Raman active symmetric stretch of $CH_4$ is 3.428 μm. Pumping with 1064 nm results in a 1$^{st}$ Stokes wavelength of 1543 mn, 2$^{nd}$ Stokes wavelength of 2.808 μm and a 1$^{st}$ anti-Stokes wavelength of 0.812 μm. As discussed below, the Raman cell may be designed to suppress the buildup of the 2$^{nd}$ Stokes and 1$^{st}$ anti-Stokes wavelengths.

As seen in Equation 1, the Stokes intensity is a function of pump intensity, pressure of the gas, interaction path length, and the initial Stokes intensity. Typically, the Stokes field is initiated by the spontaneous emission of a photon and therefore the energy and spatial characteristics will fluctuate. To avoid these fluctuations the illustrated cell 22 is seeded with a stable tunable Stokes wavelength laser 31. The illustrated laser 31 may be, for example, a continuous-wave 20 mW telecom diode laser (Mitsubishi FU-68PDF/520M45B). The illustrated laser 31 has a center wavelength of 1543.73 nm and approximately 3 nm tuneability. It is coupled to a single mode, polarization maintaining, fiber which emits a near perfect Gaussian beam. The laser diode driver and associated stable temperature controller (Wavelength Electronics, WLD3343 and WTC3243; respectively) are mounted on a custom circuit board (not shown). The laser 31 can be either current or temperature tuned to match the Stokes emission line. To ease alignment, the diode output is amplified via a 1 W fiber amplifier (IPG Photonics Corp., model EAU-1-C) to 100 mW; however, the additional power provides little to no performance enhancement. The output from the laser fiber is expanded and collimated to match the pump beam diameter, 6 mm, and spatially overlapped by transmitting through the back of the mirror 28, which, in the illustrated implementation, is a gimbal mounted turning mirror.

The source pump laser beam is reduced in diameter from the 9 nm source beam to a 6 mm diameter beam by beam compressor, which may be in the form of a Galilean telescope. The Galilean telescope is composed of two 25.4 mm diameter lenses; one plano-convex and one plano-concave, separated by 12 cm. In particular, the plano-convex lens may be a commercially available lens marketed under the name CVI Part No. PLCX-25.4-180.3-UV-1064 and the plano concave lens may be a commercially available lens marketed under the name CVI Part No. PLCC-25.4-128.8-UV-1064. The resulting beam is substantially collimated rather than focused. That is, the rays of the beam are substantially parallel rather than converging relative to any of the optics of Raman cell 22. It is further noted that the pairing of the folding mirrors 26 and 28 allows for improved circularity of the beam entering the Raman unit 22.

Figure 3:
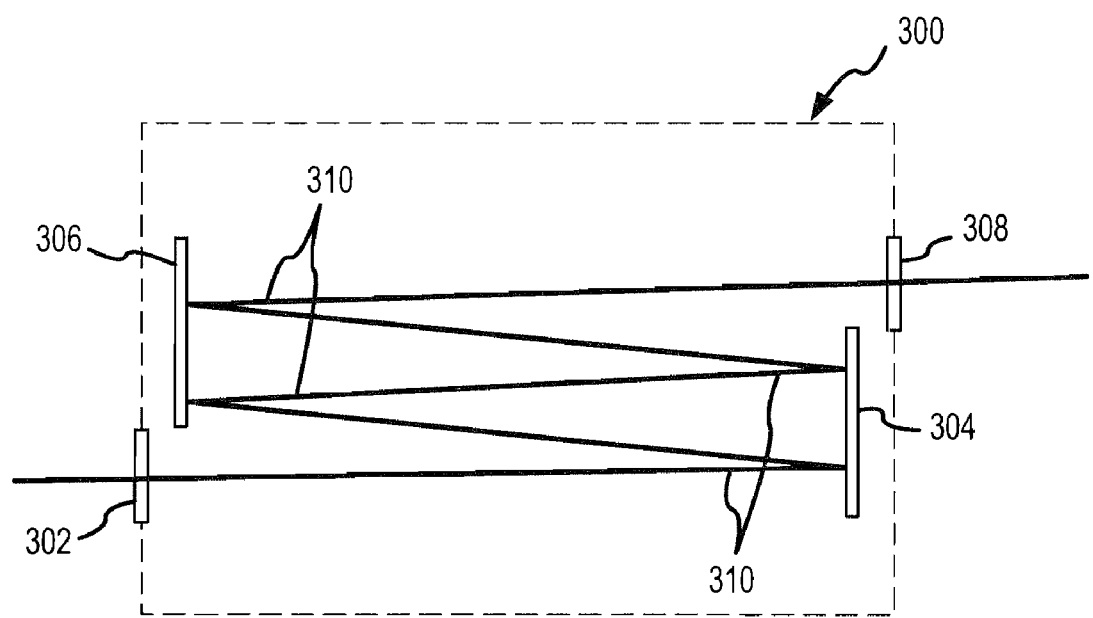
FIG. 3 is a schematic diagram illustrating an alternative Raman cell geometry in accordance with the present invention.

A number of implementations for the Raman cell are possible in accordance with the present invention. One such implementation is schematically illustrated in FIG. 3. The illustrated cell 300 includes an entrance window 302 for allowing transmission of the source beam together with the seed beam into the interior space of the cell 300, a first internal mirror 304, a second internal mirror 306 and an exit window 308 for allowing transmission of the wavelength shifted beam out of the interior space of the cell 300. The mirrors 304 and 306 are dimensioned and are angularly movable so as to allow for single or multi-pass transmission of the beam through the cell. In this regard, single pass refers to a single reflection from each of the mirrors 304 and 306 and multi-pass involves multiple reflections off of each mirror 304 and 306. In this manner, the overall pathlength of the beam within the Raman cell 300 can be changed to achieve optimal wavelength conversion.

The illustrated Raman cell 300 is dimensioned to accommodate windows 302 and 308 in end caps that provide 25.5 mm clear entrance and exit apertures as well as 50.8 mm diameter internal mirrors. In this regard, the Raman cell may be defined by a cylinder having a 20 cm outside diameter. The windows 302 and 308 are 12.7 mm thick and 38.1 mm in diameter, are made of UV-grade fused silica, and have an anti-reflection coating at least for the 1.543 micron wavelength. As will be discussed below, for implementations where it is desired to transmit both the laser pump wavelength of 1064 nm and the eye-safe 1.543 micron wavelength, the windows 302 and 308 may have an anti-reflection coating for each of the noted wavelengths.

The internal mirrors 304 and 306 are held by a single independent frame to prevent pressure changes from altering the optical path of the system. The mirrors 304 and 306 have a high reflectivity coating for the 1.543 micron wavelength (and optionally also for the 1064 nm wavelength) at 0 degrees angle of incidence. They also feature high transmission at the second Stokes line (2.8 micron) and the first anti-Stokes line (0.81 micron) to suppress shifting to these wavelengths. The total exterior length of the cell is 75 cm and the distance between the internal mirrors is 65 cm. For enhanced wavelength shifting and reduced sooting, it is desirable to circulate the methane gas in the cell. Although not shown, an electrical feed-through in the illustrated cell drives an array of a 24 volts DC axial fans inside the cell to circulate the methane. In this manner, the gas heated by preceding laser pulses is cleared out of the beam path.

The mirrors 304 and 306 are mounted on gimbals to allow for the noted adjustment as between single pass or multi-pass operation of the cell without adjusting other mirrors in the transmit path. In this regard, the mirrors may be adjusted to allow an optical path within the cell having, for example, three, five, or seven segments relative to the length of the cell.

Although the illustrated cell 300 has been utilized to provide good results, certain operational difficulties and optical inefficiencies have been noted. First, the windows 302 and 308 are anti-reflection (AR) coated to prevent losses each time the beam passes through a window and the mirrors are high-reflection (HR) coated. Second, the internal mirrors 304 and 306 are substantially parallel and therefore the beam path is slightly overlapped with itself in front of each mirror 304 or 306 as indicated by arrows 310. The AR and HR coatings are problematic for two reasons: (1) they can be damaged from the intense laser light and (2) they chemically react with gases such as methane in the presence of intense laser light. In this regard, it has been found necessary to replace the windows 302 and 308 and mirrors 304 and 306 periodically due to coating burns and significant scattering losses have been observed where the air coating has been etched away. The overlap 310 results in reduced conversion efficiency due to a reduction in the total volume of gas illuminated.

Referring again to FIG. 2, the illustrated Raman cell 22 includes a number of enhancements in this regard. The illustrated cell 22 includes an entrance window 32, internal reflectance elements 34-37 and an exit window 38. The entrance and exit windows 32 and 38 are oriented at the Brewster angle with respect to the incident beam to eliminate the need for the vulnerable AR coatings. The Brewster angle is the angle at which light, in a particular linear polarization state, will pass through an interface without any reflection. The internal reflectance elements 34-37 provide for internal rather than surface reflection of the beams. For example, the elements 34-37 may be prisms. The elements 34-37 thus redirect the light based on total internal reflections thereby eliminating the need for special HR coatings. In addition to having a higher damage threshold, the total internal reflection has negligible loss whereas the HR coatings may leak up to 5% of the pulse energy at each reflection. The elements 34-37 are also oriented at Brewster angles relative to the incident beams to eliminate the need for AR coatings on their front entrance and exit surface. Moreover, the use of the internal reflectance elements 34-37 eliminates the beam overlap geometry associated with surface reflecting mirrors. That is, by translating the beam within the elements 34-37 and then maintaining the beams in a parallel relationship within the cell 22, a larger volume of gas is illuminated for higher total gain while requiring slightly less total volume in the cell 22. The windows 32 and 38 and internal reflectance elements 34-37 may be made of, for example, infrared grade fused silica so that they can be used at any wavelength from the ultraviolet to the near infrared. The elimination of the AR and HR coatings means the illustrated cell 22 can be used at various wavelengths and will be more durable. The higher order Stokes and anti-Stokes lines can be suppressed by other means, e.g., by controlling cell gas pressure and by injection seeding.

Although the Raman cell 22 is illustrated as part of the REAL system 10, it is anticipated that the cell 22 will have utility in a variety of applications. For example, it is anticipated that the cell 22 will allow for an eye-safe water vapor DIAL at approximately a 1.5 micron wavelength. In this regard, such a DIAL may utilize an 800-900 nm pump and relatively low pressure hydrogen. The pump beam would be shifted to 1200-1570 nm via first Stokes stimulated Raman scattering. There are many water vapor absorption lines in this vicinity. It is noted in this regard that hydrogen is a higher gain medium than methane and it is therefore anticipated that only 1-2 atm of pressure would be required compared to the approximately 10-13 atm of methane that are currently used in the illustrated application. Lower gas pressure is generally safer and it is further noted that the higher Stokes and anti-Stokes lines are suppressed at such low pressure configurations.

The illustrated Raman cell may provide enhanced performance for certain aerosol backscatter lidar applications. In particular, the illustrated transmitter 12 operates at 10 Hz using a laser pump 20 with 800 mJ/pulse to produce about 200 mJ/pulse at the eye-safe wavelength of 1.543 microns. By comparison, the Scanning Aerosol Backscatter Lidar (SABL) available from the National Center for Atmospheric Research (NCAR) provides a single shot energy for each pulse that is several times lower than the illustrated system. However, the pulse repetition frequency of the illustrated system is approximately six times less than that of the SABL. For scanning applications, high pulse repetition frequency is very important because it translates directly to the angular resolution of the scan data. Thus, the illustrated cell 22 could alternatively be used with an alternative pump laser running at 50-100 Hz with 1.2 J/pulse for an eye-safe aerosol lidar with unprecedented spatial resolution and range. The illustrated cell 22 accommodates such operation because the windows 32 and 38 and internal reflectance elements 34-37 do not require fragile coatings that may not survive the more intense energy of the higher pulse repetition frequency pump.

The illustrated Raman cell 22 may also be pumped with a wavelength tripled commercially available Nd:YAG to produce multiple wavelengths in the ultraviolet range for an ozone DIAL.

Figure 4:
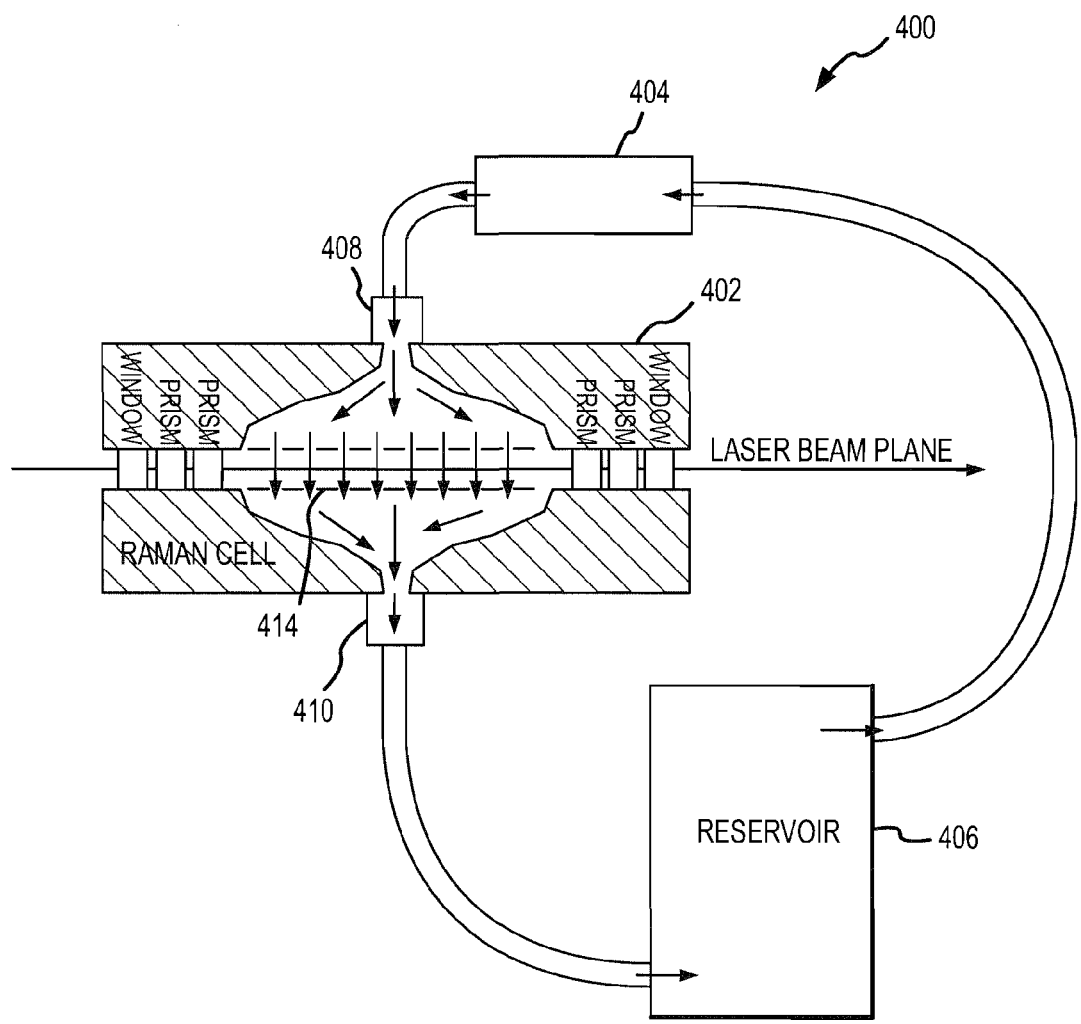
FIG. 4 illustrates a methane gas circulation system for use in connection with a Raman cell of the system of FIG. 2.

As noted above, it is desirable to circulate the gas, e.g., methane, in the Raman cell so as to avoid illuminating gas that remains heated from a preceding laser pulse. FIG. 4 illustrates a gas circulation system for circulating a Raman cell gas such as methane. The Raman cell including internal prisms and windows is schematically illustrated at 402. The circulation system 400 is used to safely circulate methane. An important objective is to have the smallest volume of methane possible in the cell where the laser beam is transmitted. This is because it is desired to minimize (1) the amount of potential energy due to compression and (2) the volume of methane that could mix with air and be flammable if a window cracked or there was otherwise a leak. The illustrated system 400 also eliminates mechanical fans inside the Raman cell. This eliminates the need for electrical feed-throughs and greatly reduces the chances of contaminating the inside of the cell due to oils or outgassing of fan material. Moreover, it eliminates the need to open the Raman cell to replace a fan if one developed a problem.

In the illustrated system 400, to circulate the methane, an external pump 404 drives the methane flow in a loop. The pump 404 draws methane from a reservoir 406 and drives it through the cell 402. Pressure sensitive valves 408 and 410 on the Raman cell 402 isolate the rest of the system if a leak were to occur in the Raman cell 402. The methane flow space through the cell 402 may be configured for improved laminarity of flow at the location of illumination. Additionally, flow grates 412 and 414 may be disposed on opposite sides of the illumination area for improved laminarity and one directional flow.

Referring again to FIG. 2, the beam 40 exiting the Raman cell 22 generally includes two wavelength components. Specifically, not all of the optical energy is converted from the source laser pump wavelength to the Raman shifted, eye-safe wavelength. It is often desired to transmit only the eye-safe wavelength into the atmosphere. Accordingly, it mat be desired to remove the source laser pump wavelength component. In the illustrated embodiment, a wavelength dispersive element 42, such as a Pellin Broca prism, receives the beam 40 and spatially separates the beam 40 into an eye-safe beam 44 and a source wavelength beam 46. The path of the source wavelength beam 46 is folded by mirror 48 and prism 50 to a beam dump component 52. For example, the beam dump component 52 may be a black box or other light absorber.

The eye-safe beam 44 is further processed for transmission into the atmosphere. Specifically, in the illustrated embodiment, the eye-safe beam 44 is processed by a beam expander 54 to impart desired beam characteristics. In this regard, it is desirable to expand the eye-safe beam 44 to provide the desired optical density as well as to improve the beam divergence.

The divergence of a laser beam is given by:

$$\Theta = M^2 \frac{2\lambda}{\pi \omega_o} \qquad (3)$$

where $\omega_o$ is the beam waist radius, $\lambda$ is the wavelength, and $M^2$ is defined as the ratio of the beam's divergence to that of a diffraction limited beam of the same waist diameter. Note from Equation 3 that the beam divergence can be reduced by improving the beam quality and/or increasing the beam diameter (beam expansion). The illustrated REAL system 10 capitalizes on this Gaussian beam propagation concept in the transmitter design to reduce the divergence of the transmit beam to fit within the receiver's field of view. First, as noted above, the Raman cell is injection seeded to improve beam quality, and second, the beam is expanded prior to transmitting into the atmosphere.

In the illustrated transmitter, the eye-safe beam 44 is expanded by expander 54, for example, in the form of a Galilean telescope. Specifically, the illustrated expander 54 is a custom lens system including two air-spaced doublets each antireflection coated for the eye-safe wavelength of 1.543 microns (and optionally for dual wavelength operation as discussed below for 1064 nm). The first 25.4 mm diameter doublet is a negative lens with a focal length of 138 mm. The second 101.6 mm diameter doublet is a positive lens with a focal length of 574 mm. The doublets are separated by 38 cm and expand beam 4.3 times. The expanded Stokes beam (about 50 mm diameter) has a half angle divergence of 0.20× 0.24 mrad. The resulting expanded, low divergence eye-safe beam is transmitted via a folded path into the atmosphere. Specifically, the path of the beam is folded by folding mirrors 56-59, each of which is coated for high reflection at the desired wavelength or wavelengths.

In the illustrated embodiment, the transmitted beam 14 is transmitted on a path that is coaxial with the backscattered radiation 18. It has been determined via ray tracing that such a coaxial transmit/receive configuration desirably achieves full overlap at 500 meters range with small -detectors. Such a coaxial configuration is achieved in the illustrated embodiment by transmitting the beam 14 off the back of the telescope secondary, as will be described below. The expanded beam size is therefore preferably limited to the secondary diameter. In this regard, the mirrors 56-59 of the illustrated embodiment are gold-coated 101.6 mm diameter mirrors at 45 degree angles of incidence. Alternatively, dielectric coatings may be used. The edges of the Stokes beam are clipped slightly in this regard. For a 99% transmission of a true Gaussian beam profile, the mirrors 56-59 would need to be 5 mm larger. The final mirror 59, mounted on the back of the telescope secondary, uses electronically controlled motors, marketed under the name New Focus Picomotors to precisely steer the transmit beam to an angle that is within the receiver field of view. Feedback servo-control based on detector readings may be utilized to optimize steering in this regard.

The illustrated receiver 16 generally includes a telescope 60, output optics 62, a detector 64, and amplifier 68 and a digitizer and computer unit 70. Each of these components is described in turn below. The telescope 60 includes a primary mirror 72 and secondary mirror 74. The illustrated telescope 60 is a Newtonian telescope with gold-coated mirror surfaces to provide approximately 90% transmission at 1.5 microns. Another option for the telescope 60 is a 40.6 cm diameter at/10 Schmidt-Cassegrain telescope (Meade LX 200 EMC). The noted Schmidt-Cassegrain telescope with gold-coated surfaces provides a transmission of about 72%. Dielectric coatings may alternatively be used in this regard.

The illustrated telescope 60 is mounted in a fixed vertical position. The system 10 may be utilized in this configuration to obtain vertical images or a scanning system may be disposed in front of the telescope for scanning applications as will be described below. In the illustrated system 10 the backscattered light collected by the telescope 60 is collimated by collimating lens 76 which may be, for example, a 25.4 mm diameter doublet lens. Such collimation facilitates transmission through an interference filter 78. The interference filter 78 provides wavelength-dependent filtering to reject noise that could otherwise compete for the dynamic range of the receiver 16. The illustrated filter 78 is a narrow bandpass interference filter (Omega Optical, Inc. 25.4 mm diameter, 1543.3 nm center wavelength, 5 nm FWHM, with at least 80% transmission). The illustrated receiver 16 further includes a focusing lens 80 for focusing the backscattered radiation onto the active surface of the detector 64. The detector 64 includes a high gain medium for detection of 1.5 micron wavelength backscatter radiation. A preferred detector for this application is an InGaAs detector. The detector used to obtain the results presented below was a 200 micron diameter InGaAs/InP avalanche photodiode (Perkins Elmer/EG & G Model No. C30662) with 75% quantum efficiency, a maximum useable gain of approximately 20 and a bandwidth of 200 MHz. More preferably, a detector amplifier unit may be utilized (Perkins Elmer/EG&G Model No. C30659-1550-R2A).

This detector drives the design of the focusing lens 80. The illustrated lens is a three element design, a doublet with companion meniscus lens, with an 18 mm focal length and 12.4 mm diameter. The lens is designed to collect all light within a 0.15 mrad FOV onto the detector for the range 500 m to 15 km. In practice, the useful range of the instrument is slightly adjustable, analogous to the depth of field of a camera. For example, by moving the position of the detector with respect to the effective focal point of the receiver, the full overlap region can be shifted in either direction. Therefore, the results presented below have minimum ranges between 350 m and 750 m. The detector 64, in a shielded enclosure, is mounted on a high precision 3-axis translation stage (Newport ULTRA Line 561D xyz) for adjustment.

The half angle FOV for the illustrated receiver 16 can be given as the photodetector radius divided by the focal length of the receiver system. In one implementation, the effective focal length of the receiver (telescope and custom optics) was calculated to be 367 mm at 1.543 microns. Therefore the receiver FOV, with a 200 micron diameter detector, is 0.27 mrad (half angle). This receiver FOV is slightly larger than the divergence of the transmitted beam 14 which, as noted above, is about 0.20×0.24 mrad.

The detector 64 provides an electrical output signal that is representative of the optical signal incident on the detector surface. This output signal is then amplified by amplifier 68. In the illustrated embodiment, the amplifier 68 is an operational amplifier (Analog Devices Model ADA29) that has a bandwidth of 55 MHz at a gain of 20. The op amp, photodiode, and power supply are mounted on a customer circuit board in an RF shielded case. In order to amplify return signals that are near the noise level of the detector 64 the noted amplifier 68 is operated with a gain of approximately 850. Unfortunately, this reduces the bandwidth to approximately 1 MHz (350 ns rise time). Operated in this manner, the bandwidth of the amplifier becomes the limiting factor with regard to range resolution. Range resolution can be enhanced in this regard by providing a second stage amplifier.

More specifically, several factors can limit the range resolving capability of a backscatter lidar system. First is the laser pulse length. The 1543 mm pulse duration is 4 ns which corresponds to 1.2 m in space. Next, the bandwidth (responsiveness) of the photodetector and amplifier must be considered. The InGaAS APD used to produce the results presented below has a bandwidth of 200 MHz with an equivalent rise time of 1.8 ns which corresponds to approximately 30 cm in range. However, as stated earlier, the bandwidth of the illustrated single stage amplifier is 1 MHz with an equivalent rise time of 350 ns which corresponds to approximately 53 m in range. The detector-amplifier unit noted above has a bandwidth of 50 MHz corresponding to a range resolution of about 1.1 m for single channel operation or less than 3 m for dual channel operation. Lastly, the digitizer sampling rate controls the spacing of the data points although they may not be independent samples due to one of the slower previous components. The current digitizer, as described above, is capable of 100 MSPS in single-channel mode or 50 MSPS dual-channel mode. 50 MSPS is equivalent to 3 m spatial sampling. Therefore, although the data shown have pixels every 3 m in range, the resolution is 53 m. In other words, the illustrated single-stage amplifier implementation oversamples the backscatter signal. The noted two-stage amplifier allows for realization of potential range resolution on the order of 3 m or better. The lidar system of the present invention also yields a signal-to-noise ratio of greater than 10 (taking into account the detector noise, background noise from sky radiance and background noise from molecular scattering) at a distance of 15 km for a single laser pulse (or integration time of less than 0.1 seconds) when pointing at an elevation of less than 5° through low altitude haze. The system specifications are set forth in Tables 1 and 2 below.

TABLE 1

Instrument Characteristics

| characteristic | value |
|---|---|
| Transmitter | |
| Wavelength | 1543 nm |
| Energy output | 220 mJ |
| PRF (max) | 10 Hz |
| Divergence (half angle) | 0.20 × 0.24 mrad |
| $M^2$ of Nd:YAG pump | 3 × 3 |
| $M^2$ of Stokes beam | 10 × 12 |
| Diameter of transmitted beam | 50 mm |
| Pulse duration | 4 ns FWHM |
| Receiver | |
| Telescope | 40-cm diameter |
| Field of View (half angle) | 0.27 mrad |
| Filter Bandwidth | 5 nm |
| Detector | 200 μm InGaAs:APD |
| A/D sample rate | 50 MHz |
| A/D resolution | 14 bits |

TABLE 2

Factors influencing range resolution

| Characteristic | Frequency | Time | Equivalent range resolution |
|---|---|---|---|
| Pulse duration | | 4 ns | 1.2 m |
| InGAAs APD response | 200 MHz | 1.8 ns | 0.3 m |
| Amplifier response | 50 MHz | 7 ns | 1.1 m |
| Digitizer sampling | 100 MSPS | | 1.5 m |

The analog output of the amplifier is converted to a digital signal by an analog-to-digital card (GAGE Model 14100) in the digitizer and computer 70, which may be, for example, a personal computer. The digitizer card is capable of 14 bit quantization. It is also capable of recording one channel at 100 megasamples per second (MSPS) or two channels at 50 MSPS. Programs may be provided in Labview to display the backscatter data in real-time and write files to the hard disk. In addition to acquiring backscatter data, the Labview program is capable of simultaneously monitoring laser energy's location and the temperature and pressure inside the Raman cell via the serial connections. The Labview programs thereby provide backscatter images as presented below. In addition, such programs can provide for integration of images over a scanning range of interest to provide integrated volume imaging.

Figure 5:
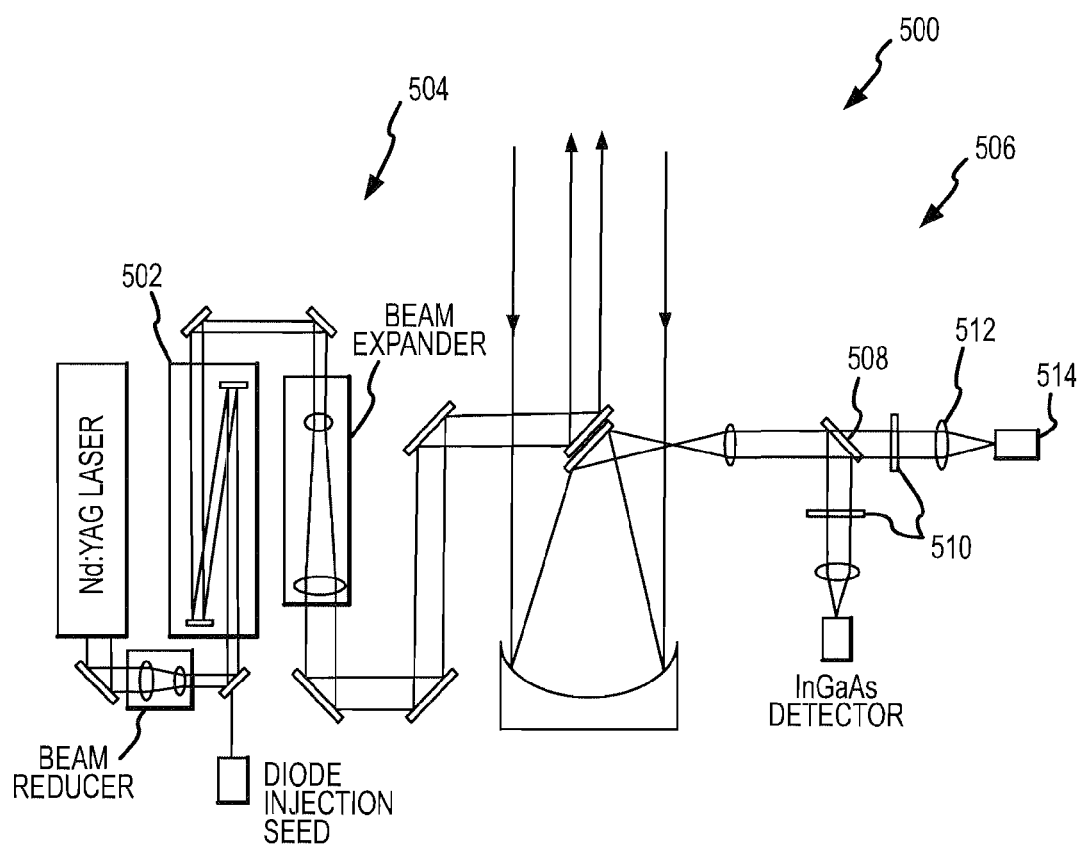
FIG. 5 is a schematic diagram illustrating an alternative embodiment of an atmospheric aerosol lidar system in accordance with the present invention.

FIG. 5 illustrates an alternative implementation of a lidar system 500 for dual wavelength operation. Many of the components of the system 500 are identical to the corresponding components described above and such description will not be repeated, for the sake of brevity. A few differences are noted, however. First, the Raman cell 502 is a mirror-based Raman cell as described above in connection with FIG. 3. Second, the wavelength dispersion element and beam dump element as described above are eliminated such that the transmitter 504 transmits both the source laser pump wavelength component and the eye-safe Raman-shifted wavelength component into the atmosphere. Although this multicomponent beam is not eye-safe, such dual wavelength operation may be desired for calibration purposes or for our certain research applications. To accommodate such transmission of beams that are not eye-safe, the system 500 may be operated in conjunction with a conventional radar system to identify any approaching aircraft and provide a zone of safety around the system 500.

In addition, the individual wavelength components are separately processed in the receiver 506 so that the receiver components can be optimized for each wavelength. In this regard, the illustrated system includes a wavelength separator 508, such as a short-wave-pass (SWP) dichroic (CIV) Part No. SWP-45-1540-1064-PW-2025-C) to separate the 1064 nm and 1.543 micron backscatter. The SWP dichroic has a reflectance of at least 99.5% at 1.540 microns and passes at least 80% at 1064 nm. The subsequent 1.543 micron channel processing components can be as described above. The 1064 nm channel processing components include an interference filter 510, for example, an Omega Optical Inc. 25.4 mm diameter, 1064.2 nm center wavelength, 5 nm FWHM, with at least 80% transmission to reject background light. The radiation passing through the filter 510 is focused by focusing lens 512 onto detector 514. In this regard, the detector 514 may be a 1.5 mm diameter active area, long wavelength enhanced, silicon avalanche photodiode (EG&G Model No. C30955E) in a LiCEL GbR detector package that includes a low noise preamplifier. The package includes a single element aspheric focusing lens and xyz translation stage. The receiver FOV is slightly larger for the 1064 nm channel is about 1.68 mrad. For the 1064 nm channel, the detector package uses a 10 MHz bandwidth linear transimpedance amplifier.

It will further be appreciated that the optics of the system 500 including the various windows and mirrors will include coatings optimized for both wavelength channels.

Figure 6:
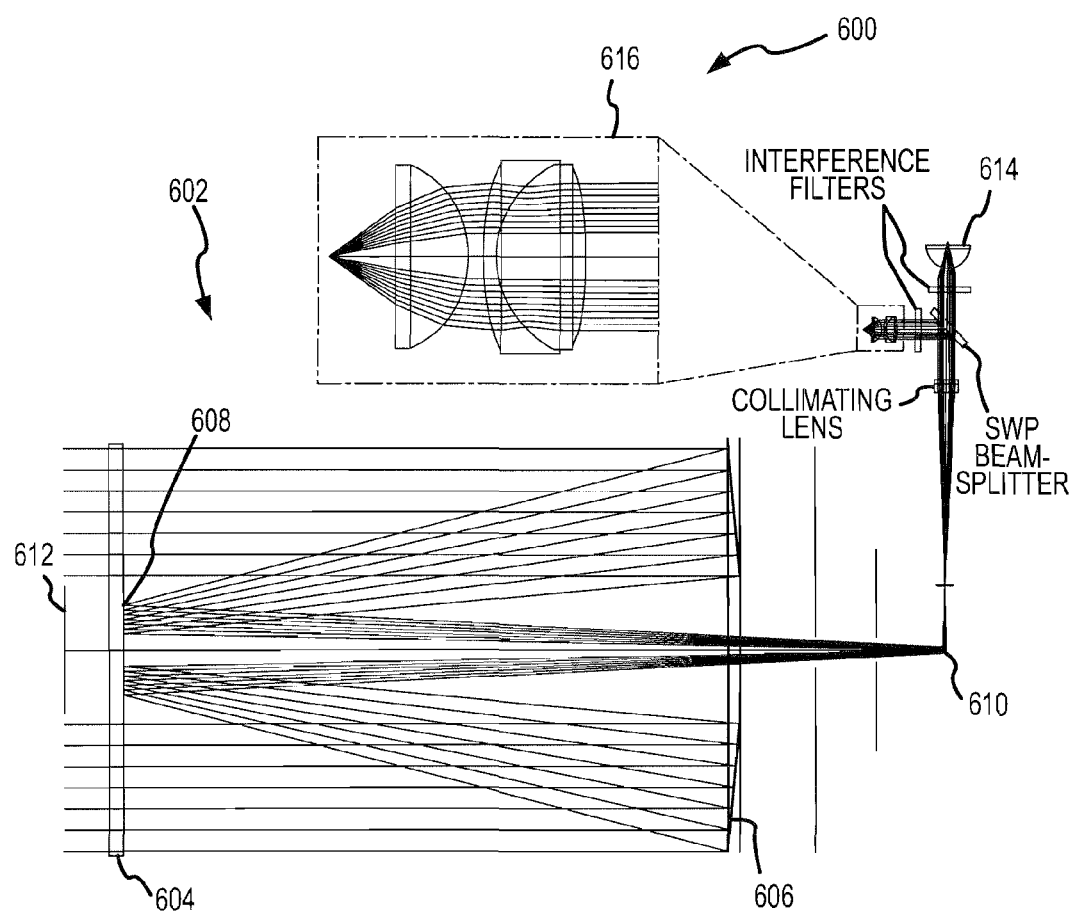
FIG. 6 is a ray trace showing optical pathways within the receiver of the system of FIG. 5.

FIG. 6 shows a ray trace for a receiver generally corresponding to that of FIG. 5. In the case of FIG. 6, the telescope 602 of the receiver 600 is a Schmidt-Cassegrain telescope including a corrector plate 604, a primary mirror 606, a secondary mirror 608 and a tertiary mirror 610. As the ray trace indicates, the secondary mirror 608 results in an area of obscuration 612. This area of obscuration 612 may be exploited to position a transmitting mirror of the transmitter for coaxial transmit/receive functionality free from optical penalty. The combined detector and focusing lens package for the 1064 nm channel is indicated is indicated as 614. As noted above, the 1.543 micron channel utilizes a custom focusing lens. This lens system is indicated with an associated ray trace in the expanded window at 616. As shown, this custom lens system provides for efficient focusing of the eye-safe channel radiation onto the small detector surface.

Figure 7:
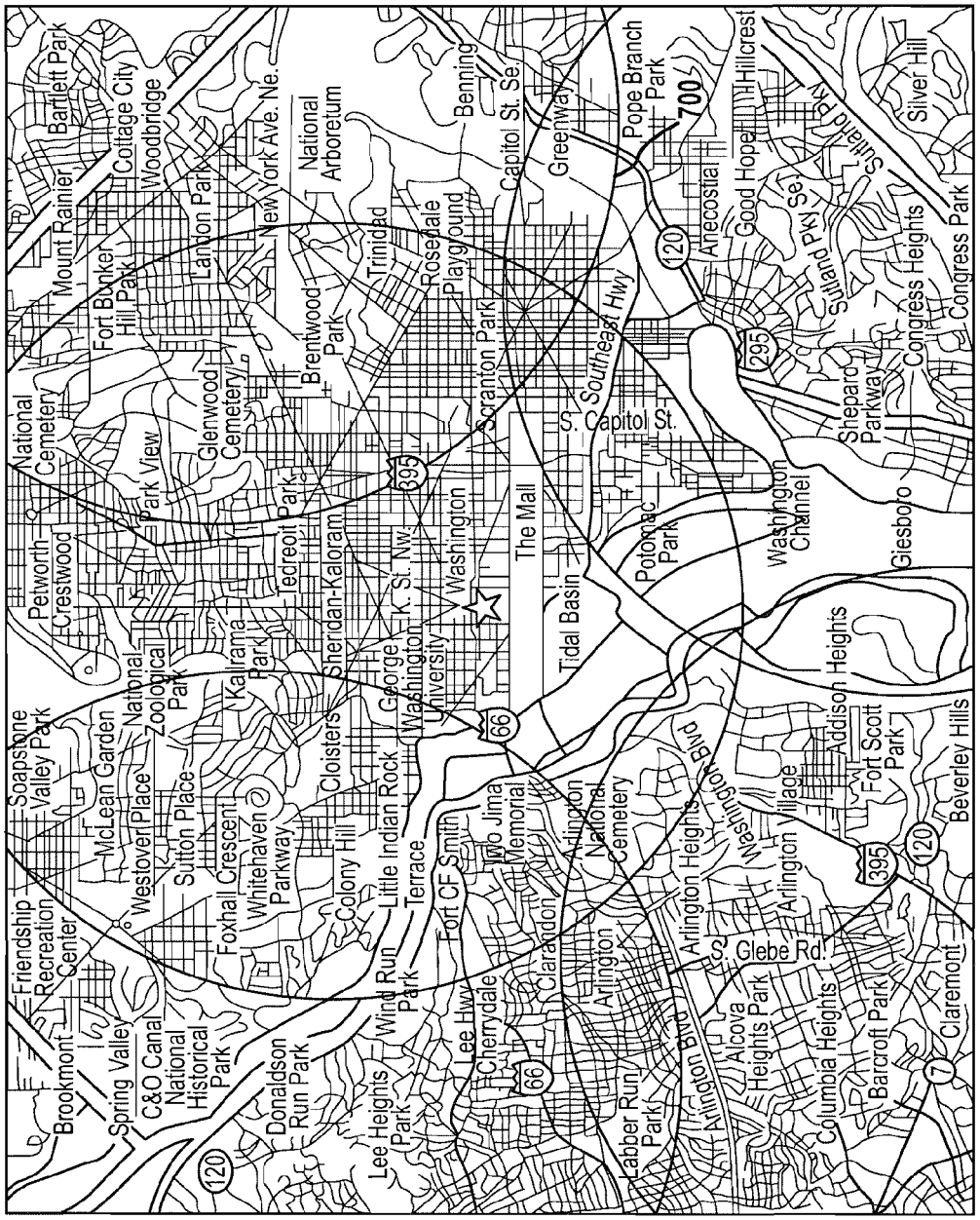
FIG. 7 is a schematic diagram illustrating a network of scanning lidar systems in accordance with the present invention.

As discussed above, for certain lidar applications it may be desired to scan the transmitted beam across an angular range relative to one or more scan axes. Such scanning capability may be desirable, for example, in connection with operating a network of lidars to monitor aerosols in the atmosphere over a metropolitan area. Such monitoring may be conducted, for example, to monitor sources of pollution or to identify and track the source of harmful agents in the atmosphere. Such a network is schematically illustrated in FIG. 7. Specifically, FIG. 7 illustrates a number of overlapping coverage areas 700, schematically illustrated as circles. It will be appreciated that the effective range of each lidar system will vary depending on a number of factors and there is not, in reality, a well-defined edge to any coverage area. However, the various components of the lidar system may be tuned to a desired coverage range. As shown in FIG. 7, the coverage areas may be overlapped to ensure that there are no gaps in coverage or to provide coverage via multiple lidar systems for areas of particular interest. Where adjacent lidar coverage areas overlap, the scanning phase of such neighboring lidar systems may be controlled to provide more frequent coverage in the area of overlap. The network of FIG. 7 corresponds to individual lidar systems that scan a full circular range relative to a vertical axis. Such scanning may be continuous. The lidar systems may also scan across a desired elevation range. In this regard, the scanning relative to the azimuth and elevation axes may be conducted in a raster pattern. The elevation scanning may extend over a 90 degree range so as to define spherical coverage region associated with each lidar system.

Figure 8:
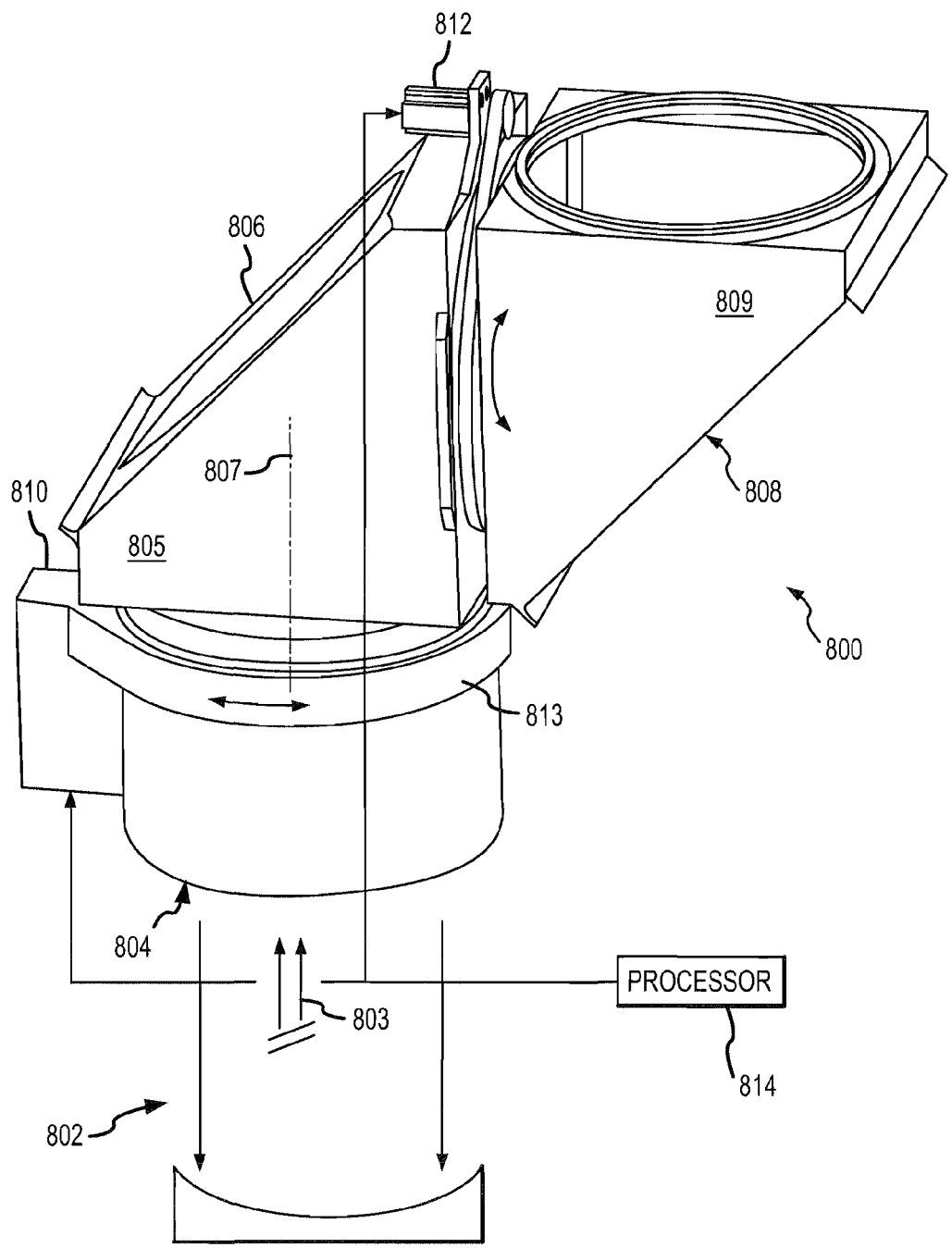
FIG. 8 is a schematic diagram illustrating a scanning system that may be used in connection with the lidar systems of FIG. 2 or FIG. 5.

FIG. 8 illustrates a scanning system 800 for accomplishing such scanning. The scanning system is disposed in front of the telescope 802 of a lidar system. Specifically, a transmitted beam 803 enters the scanning system 800 through an entrance window 804 and is reflected by a first mirror 806 mounted in a first housing section 805 that is rotatable about the telescope optical axis 807. The transmitted beam 803 is redirected by the mirror 806 to a second mirror 808 mounted in a second housing section 809 that is rotatable with respect to the first housing section 805 about an optical axis connecting the mirrors 806 and 808. The combined action of the two mirrors 806 and 808 allows for directing the beam 803 to any desired elevation angle and azimuth angle. The returning backscatter radiation is routed to the telescope 802 by the reverse pathway. It will be appreciated that the mirrors 806 and 808 are movable in a coordinated fashion to direct the transmitted beam and backscatter radiation in this regard. Specifically, a pair of movable mirrors 806 and 808 are used in this regard for enhanced beam circularity and optical efficiency. Moreover, because each mirror 806 or 808 is at a fixed angle relative to the incident beams, the beam footprint on the mirrors does not change and is minimized relative to the full range of scanning angles. The mirrors are driven across the desired range of angular motion by respective azimuth and elevation motors 810 and 812. These motors may be driven by drive signals from the processor 814. The corresponding elevation and azimuth values are recorded by software running on the processor 814 for compiling and recording imaging information.

The illustrated system 800 accommodates continuous 360° azimuth scanning. In this regard, the first housing section 805 may be mounted on a slip ring mounting 813. Because of the coaxial geometry of the lidar system, a single scanning system 800 can be utilized for transmission and reception. Moreover, the illustrated system 800 allows for beam scanning without moving the transmitter and receiver components for improved efficiency and robustness.

Figure 9:
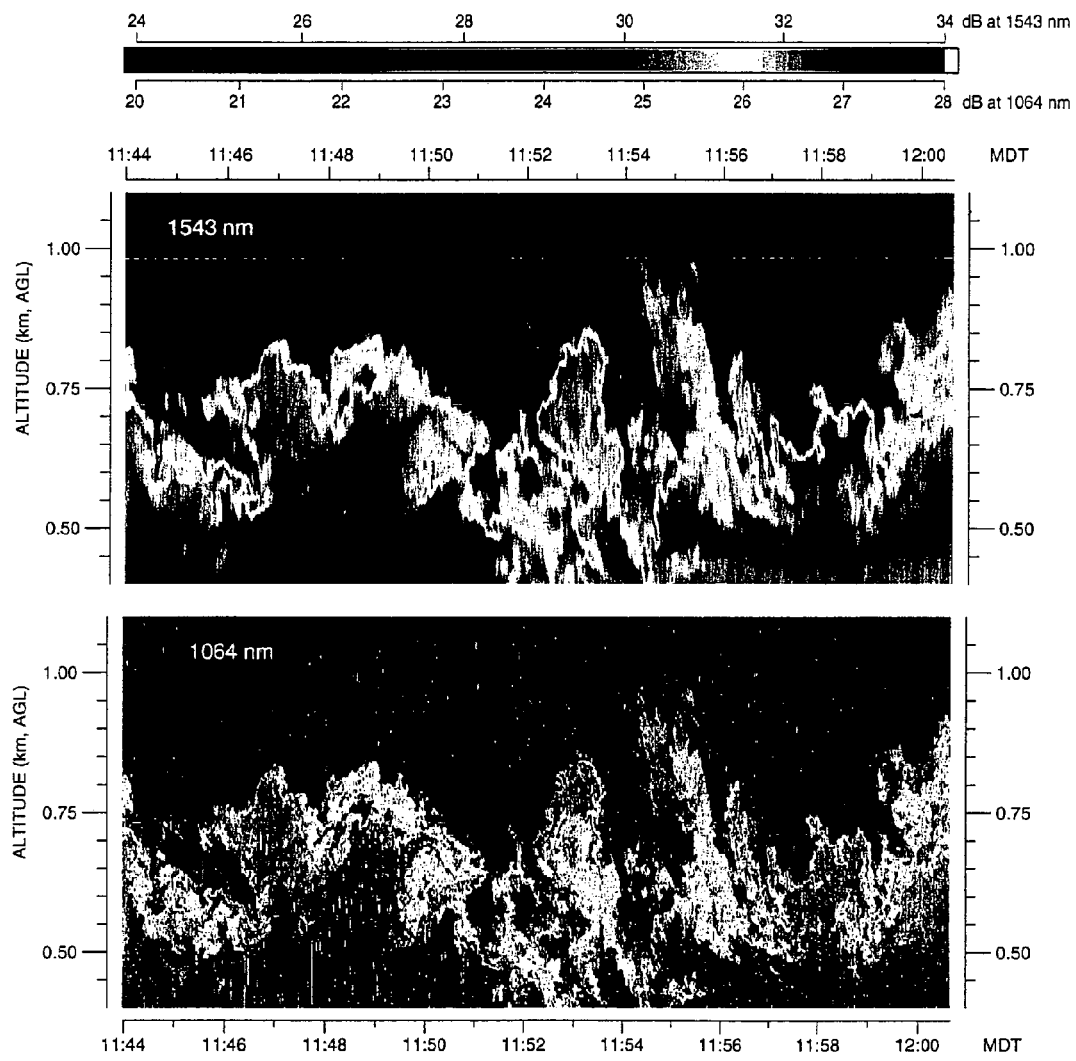
FIG. 9 illustrates time versus altitude images obtained using an atmospheric aerosol lidar system constructed in accordance with the present invention.
Figure 10:
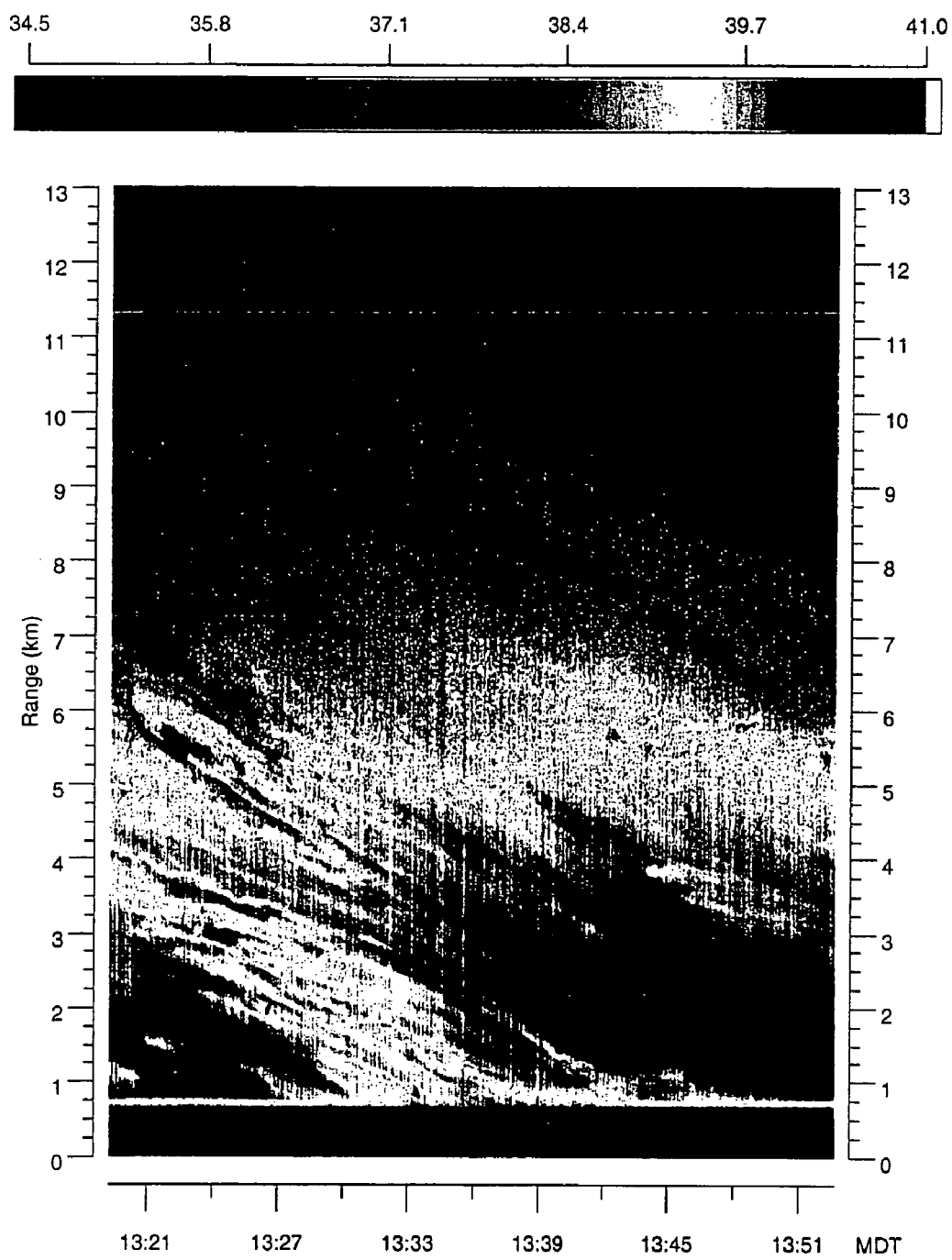
FIG. 10 illustrates time versus range images for a nonvertical beam position obtained using an atmospheric lidar system constructed in accordance with the present invention.

A lidar system was constructed according to the teachings above and operated to obtain atmospheric aerosol imaging information. The results of these tests are illustrated in FIG. 9 and FIG. 10. In the data illustrated, backscatter was averaged together from consecutive groups of ten laser shots to form 1 second averages. The backscatter signals were sampled at 50 MHz to provide data points at 3 m intervals in range. The DC baseline of each average return, which is proportional to the background intensity, is subtracted based on an average of the data point sample before the laser was fired. The average lidar return was then corrected for one-over-range-squared dependencies. The corrected backscatter intensity data are plotted in FIGS. 9 and 10 as time versus range color images.

FIG. 9 shows backscatter intensity for the 1.543 micron and 1064 nm wavelengths collected simultaneously when the beam was pointed vertically. The time span of the images is 17 minutes and the altitude range spans 700 m (from 400 m to 1100 m above ground level). Both images in FIG. 9 show the detailed vertical structure of the intrainment zone of a convective boundary layer. A visual comparison of the time-versus-height images indicates that the 1.543 micron data are smoother. This is attributed to the bandwidth difference of the amplifiers for the two channels. Despite this difference, the comparison shows excellent agreement and demonstrates the ability to resolve fine scale detail at the eye-safe wavelength of 1.543 microns. Improved range resolution is anticipated by substituting a two-stage amplifier in place of the single stage amplifier used for the 1.543 micron channel.

To estimate the useful range of the lidar when scanning in a near horizontal elevation angle, a stationary flat turning mirror was used to redirect the beam to approximately 3 degrees above horizon. For these tests, only the eye-safe wavelength was transmitted. FIG. 10 shows backscatter from a 33 minute period when the beam was directed to the NNE with a 3 degree elevation angle. Consecutive groups of ten laser shots were averaged to form 1 second averages. The backscatter signal was sampled at 50 MHz to provide 3 m pixels. The figure shows coherent aerosol structures from about 750 m to over 9 km range. The height of the laser beam is estimated to be about 470 m above the surface at 9 km range neglecting variations in the train. The flat turning mirror mount had an aperture of 35.5 cm. Therefore, the full collection efficiency of the 40.6 cm telescope was not utilized and the backscatter signal was reduced by about 25%. These tests demonstrate the feasibility of an eye-safe scanning lidar system.

Figure 11:
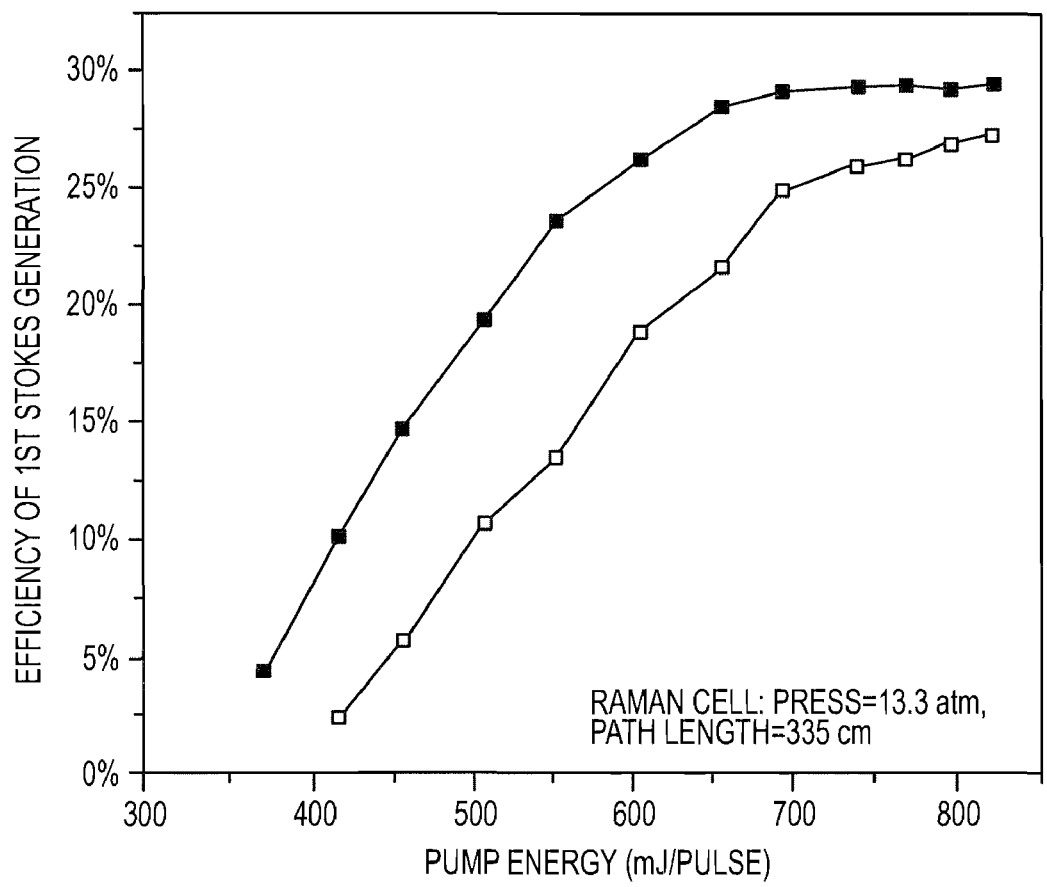
FIG. 11 illustrates the optical efficiency of a transmitter constructed in accordance with the present invention as a function of input pump energy.
Figure 12:
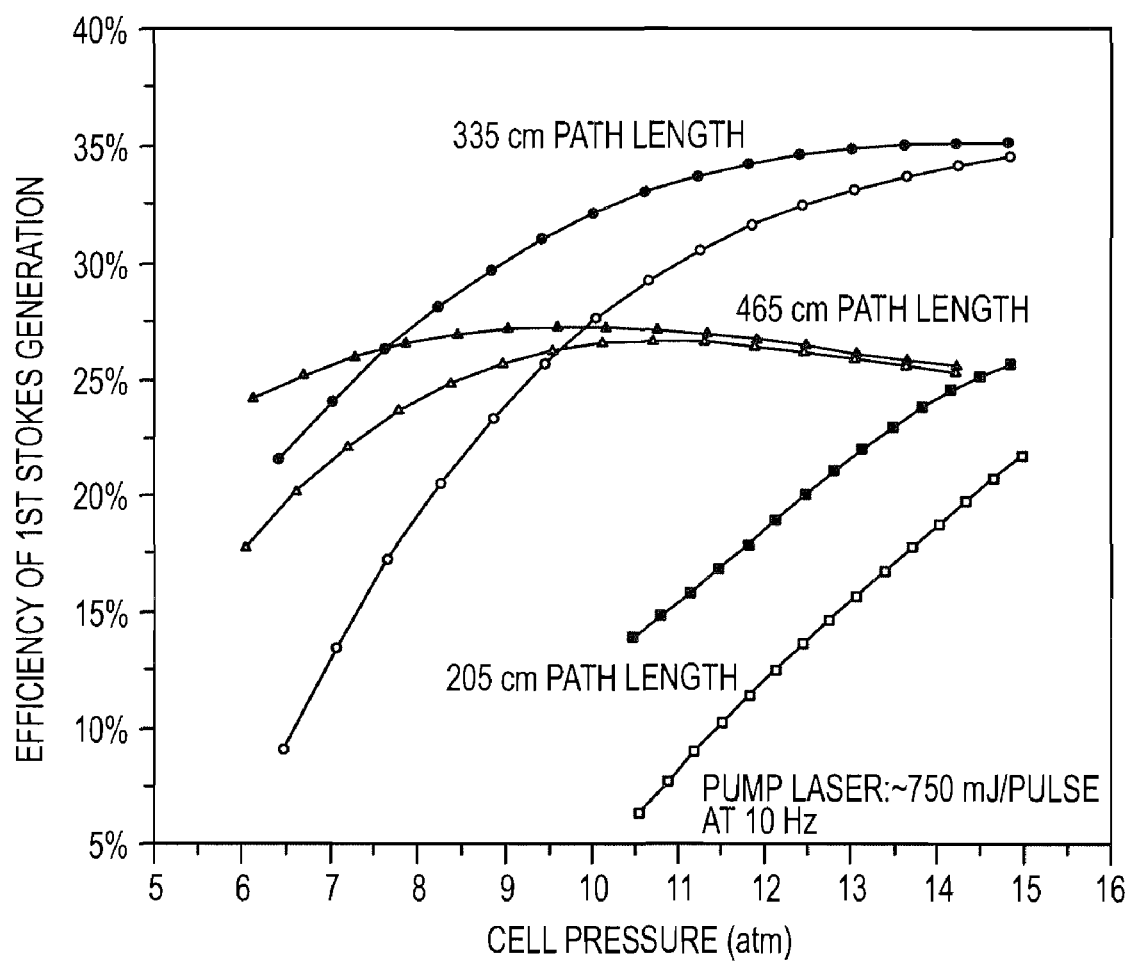
FIG. 12 illustrates the optical efficiency of a transmitter constructed in accordance with the present invention as a function of Raman cell pressure for three different Raman cell path lengths.
Figure 13:
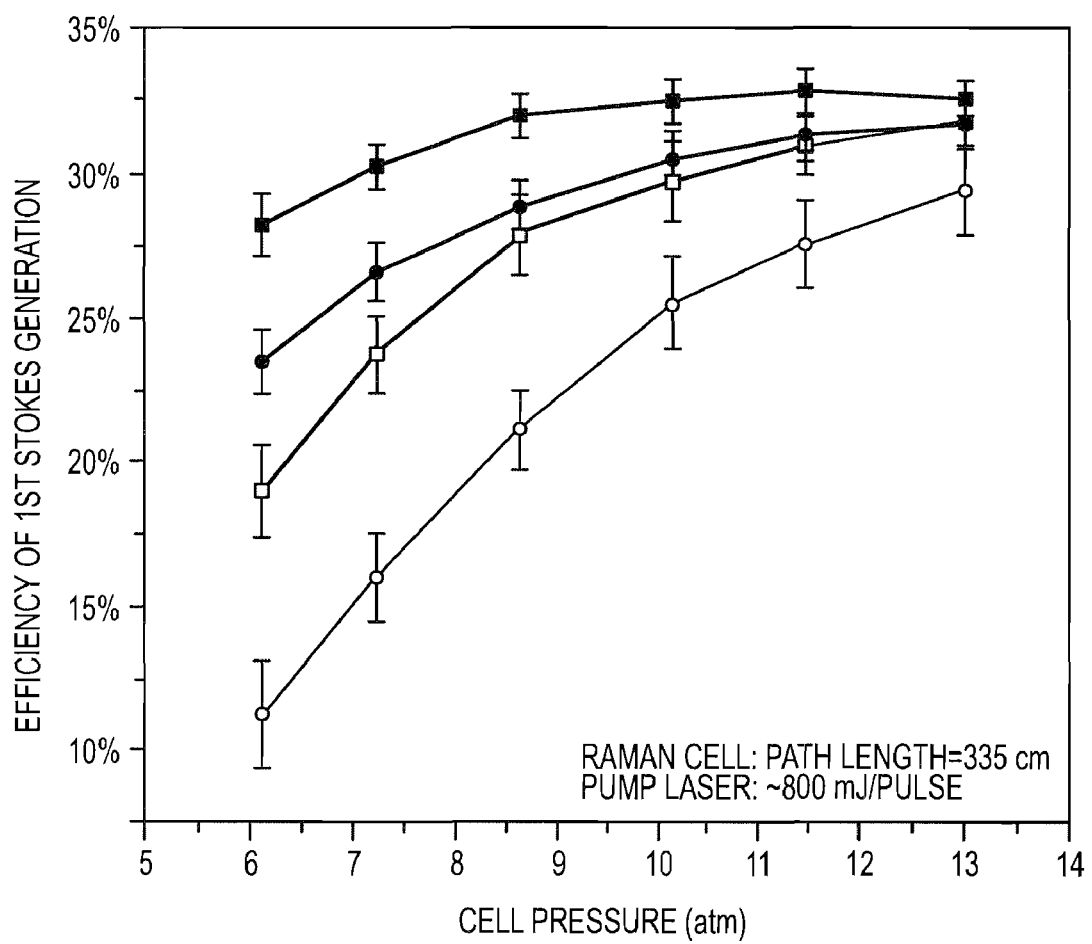
FIG. 13 illustrates the optical efficiency of a transmitter constructed in accordance with the present invention as a function of cell pressure for different pulse repetition frequencies.

FIGS. 11-13 illustrate how various parameters affect the efficiency of the Raman cell operation. In particular, FIG. 11 illustrates input pump energy versus Stokes energy conversion efficiency. The solid and hollow symbols represent the injection seeder on and off, respectively. In this case, it is assumed that the Raman cell has a gas pressure of 13.3 atm and the cell is configured to provide an illumination pathlength of 335 cm. As shown, the seed laser provides a significant increase in Stokes energy conversion efficiency for given parameters.

FIG. 12 illustrates the Stokes energy efficiency versus Raman cell pressure. Three gain lengths are shown for three, five and seven configurations. The solid and hollow symbols represent the injection seeder on and off, respectively. In this case, the pump energy was 750 mJ/pulse with a pulse length of 6 nsec. Again, a significant increase in Stokes energy conversion efficiency is achieved by seeding, though the benefit obtained by seeding is somewhat dependent on pathlength. Moreover, in general, it can be observed that the Stokes energy conversion efficiency improves with higher cell pressure. However, a desired level of Stokes energy conversion efficiency can be achieved at significantly reduced pressures by way of seeding as illustrated.

FIG. 13 illustrates Stokes energy conversion efficiency versus Raman cell pressure. Two pulse repetition rates are shown where the square symbols indicate a 5 Hz repetition rate and the circles indicate a 10 Hz repletion rate. The arrow bars represent the standard deviation of 600 shots. The solid and hollow symbols represent the injection seeder on and off, respectively. In this case, the pump energy was 700 mJ per pulse for a 6 nsec pulse. As shown, a significant increase in Stokes energy conversion efficiency is achieved at lower repetition rates. However, the increase in efficiency yielded by seeding more than compensates for the difference in efficiency associated with halving the repetition rate.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A lidar system comprising:
    a transmitter for transmitting an optical beam having a primary wavelength between about 1.5-1.8 microns and having a first value of divergence, said optical beam further having a pulse repetition frequency of at least about 10 Hz and a pulse energy of at least about 100 mJ/pulse; and
    a receiver for receiving scattered radiation of said optical beam, said receiver having a second value of field of view defined by a detector surface and detector optics and a range resolution of no more than about 50 meters;
    wherein said second value of field of view of said detector subsystem is at least about as great as said first value of divergence of said transmitter subsystem.

2. A lidar system as set forth in claim 1, wherein said transmitter comprises a laser pump for providing a source beam having a source wavelength different than said primary wavelength and a wavelength shifter for shifting said source beam from said source wavelength to said primary wavelength.

3. A lidar system as set forth in claim 2, wherein said wavelength shifter comprises a Raman wavelength shifter.

4. A lidar system as set forth in claim 3, wherein said Raman wavelength shifter includes at least one internal reflectance element for redirecting said beam within a housing of said Raman wavelength shifter substantially free from surface reflection.

5. A lidar system as set forth in claim 3, wherein said Raman wavelength shifter comprises at least one optical element disposed at a Brewster angle with respect to said beam.

6. A lidar system as set forth in claim 3, wherein said transmitter further comprises a seed laser for providing a seed beam for transmission to said Raman wavelength shifter together with said source beam.

7. A lidar system as set forth in claim 6, wherein said source beam and said seed beam have substantially equal beamwidths and are arranged for substantially coaxial transmission to said Raman wavelength shifter.

8. A lidar system as set forth in claim 3, wherein said transmitter further comprises a beam compressor disposed between said laser pump and said Raman wavelength shifter for compressing said source beam from a first width to a second width less than said first width substantially free from focusing in relation to said Raman wavelength shifter.

9. A lidar system as set forth in claim 3, wherein said transmitter further comprises a gas circulation system for circulating a gas relative to a housing of said Raman wavelength shifter.

10. A lidar system as set forth in claim 9, wherein said gas circulation system comprises a gas pump disposed outside of said housing.

11. A lidar system as set forth in claim 3, wherein said transmitter further comprises a beam expander for receiving said optical beam from said Raman wavelength shifter and expanding said beam from a first beamwidth to a second beamwidth greater than said first beamwidth.

12. A lidar system as set forth in claim 3, wherein said transmitter further comprises a filter for receiving an output beam from said Raman wavelength shifter and removing a component therefrom associated with said source wavelength.

13. A lidar system as set forth in claim 1, wherein said receiver comprises collection optics for collecting said backscattered radiation into a compressed beam, a detector for converting incident radiation into an electrical signal representative of said incident radiation, and focusing optics interposed between said collection optics and said detector for receiving said compressed beam and directing said compressed beam onto an active detector surface of said detector.

14. A lidar system as set forth in claim 13, wherein said collection optics comprises a telescope.

15. A lidar system as set forth in claim 13, wherein said receiver further comprises a collimator disposed between said collection optics and said focusing optics for collimating said compressed beam and a filter, disposed between said collimator and said focusing optics, for filtering said compressed beam on a wavelength dependent basis.

16. A lidar system as set forth in claim 13, wherein said detector comprises an InGaAs conversion medium.

17. A lidar system as set forth in claim 1, wherein said transmitted optical beam and said received scattered radiation are substantially coaxial.

18. A lidar system as set forth in claim 1, wherein said second value is between about 1.0 and 1.5 times said first value.

19. A lidar system as set forth in claim 1, further comprising a scanner for scanning said optical beam relative to at least one scan axis.

20. A lidar system as set forth in claim 19, wherein said scanner is operative to scan said optical beam relative to two axes.

21. A lidar system as set forth in claim 1, wherein said receiver comprises a processor for generating an atmospheric aerosol image based on data acquired in less than 1 second by said detector.

22. A method for analyzing atmospheric aerosols, comprising the steps of:
    transmitting a beam having a wavelength of between about 1.5-1.8 microns, a pulse energy of at least about 100 mJ/pulse, a pulse repetition frequency of at least about 10 Hz, and a first value of divergence into the atmosphere; and
    receiving backscattered radiation of said beam using a receiver having a second value of field of view at least about equal to said first value of divergence and a range resolution of no more than about 50 meters.

23. The method as set forth in claim 22, wherein said step of transmitting comprises transmitting said beam with a pulse repetition frequency of at least about 10 Hz.

24. The method as set forth in claim 23, further comprising the step of analyzing said received radiation to detect atmospheric aerosols.

* * * * *

UNITED STATES PATENT AND TRADEMARK OFFICE
CERTIFICATE OF CORRECTION

PATENT NO.        : 7,583,364 B1                                   Page 1 of 1
APPLICATION NO.   : 10/804863
DATED             : September 1, 2009
INVENTOR(S)       : Mayor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 266 days.

Signed and Sealed this

Fourteenth Day of September, 2010

David J. Kappos
*Director of the United States Patent and Trademark Office*